US009039997B2

(12) United States Patent
Cohen et al.

(10) Patent No.: US 9,039,997 B2
(45) Date of Patent: May 26, 2015

(54) MICROFLUIDIC DEVICES WITH REMOVABLE COVER AND METHODS OF FABRICATION AND APPLICATION

(75) Inventors: David Cohen, San Bruno, CA (US); Andrew May, San Francisco, CA (US); Martin Pieprzyk, Belmont, CA (US); Brian Fowler, San Mateo, CA (US); Kim Huat Lee, Singapore (SG); Jun Yan, Singapore (SG); Ming Fang Zhou, Singapore (SG); Seng Beng Ng, Singapore (SG)

(73) Assignee: Fluidigm Corporation, So. San Francisco, CA (US)

( * ) Notice: Subject to any disclaimer, the term of this patent is extended or adjusted under 35 U.S.C. 154(b) by 197 days.

(21) Appl. No.: 13/499,879

(22) PCT Filed: Sep. 29, 2010

(86) PCT No.: PCT/SG2010/000369

§ 371 (c)(1), (2), (4) Date: Apr. 2, 2012

(87) PCT Pub. No.: WO2011/040884

PCT Pub. Date: Apr. 7, 2011

(65) Prior Publication Data

US 2012/0195810 A1 Aug. 2, 2012

(30) Foreign Application Priority Data

Oct. 2, 2009 (SG) ............................... 200906624-2

(51) Int. Cl.
*B01L 99/00* (2010.01)
*B01L 3/00* (2006.01)

(Continued)

(52) U.S. Cl.
CPC ............. *B01L 3/502738* (2013.01); *B01L 7/52* (2013.01); *B01L 9/527* (2013.01); *B01L 2300/0887* (2013.01); *B01L 2300/123* (2013.01); *B01L 2400/0655* (2013.01); *G01N 1/405* (2013.01)

(58) Field of Classification Search
CPC .................. B01L 2300/0887; B01L 2300/123; B01L 9/527
USPC .................................................. 422/502, 503
See application file for complete search history.

(56) References Cited

U.S. PATENT DOCUMENTS 6,540,895 B1 4/2003 Spence et al.
6,632,652 B1 10/2003 Austin et al.

(Continued)

FOREIGN PATENT DOCUMENTS

WO WO 01/47369 A2 9/2001
WO WO 2004/089810 A2 10/2004

(Continued)

OTHER PUBLICATIONS

Thangawng et al., "Bond-Detach Lithography: A Method for Micro/Nanolithography by Precision PDMS Patterning." Small Journal, No. 1, pp. 132-138, 2007.

*Primary Examiner* — Paul Hyun
(74) *Attorney, Agent, or Firm* — Kilpatrick, Townsend & Stockton LLP

(57) ABSTRACT

The present invention includes microfluidic systems having a microfabricated cavity that may be covered with a removable cover, where the removable cover allows at least part of the opening of the microfabricated cavity to be exposed or directly accessed by an operator. The microfluidic systems comprise chambers, flow and control channels formed in elastomeric layers that may comprise PDMS. The removable cover comprises a thermoplastic base film bonded to an elastomer layer by an adhesive layer. When the removable cover is peeled off, the chamber is at least partially open to allow sample extraction from the chamber. The chamber may have macromolecular crystals formed inside or resulting contents from a PCR reaction. The invention also includes a method for making vias in elastomeric layers by using the removable cover. The invention further includes methods and devices for peeling the peelable cover or a removable component such as Integrated Heater Spreader.

31 Claims, 22 Drawing Sheets

132
130
128a
128b
136
126
124
122
138

(51) Int. Cl.

| | |
|---|---|
| ***B01L 9/00*** | (2006.01) |
| *B01L 7/00* | (2006.01) |
| *G01N 1/40* | (2006.01) |

(56) References Cited

U.S. PATENT DOCUMENTS

| | | | |
|---|---|---|---|
| 6,885,982 | B2 | 4/2005 | Harris et al. |
| 6,951,632 | B2 | 10/2005 | Unger et al. |
| 7,042,649 | B2 | 5/2006 | Quake et al. |
| 7,059,348 | B2 | 6/2006 | Nat |
| 7,062,418 | B2 | 6/2006 | Lee et al. |
| 7,097,809 | B2 | 8/2006 | Dam et al. |
| 7,161,736 | B2 | 1/2007 | Legrand et al. |
| 7,192,629 | B2 | 3/2007 | Lammertink et al. |
| 7,217,367 | B2 | 5/2007 | Huang et al. |
| 7,232,109 | B2 | 6/2007 | Driggs et al. |
| 7,248,413 | B2 | 7/2007 | Quake et al. |
| 7,262,923 | B2 | 8/2007 | Quake et al. |
| 7,279,146 | B2 | 10/2007 | Nassef |
| 7,291,512 | B2 | 11/2007 | Unger |
| 7,294,503 | B2 | 11/2007 | Quake et al. |
| 7,368,163 | B2 | 5/2008 | Huang et al. |
| 7,442,556 | B2 | 10/2008 | Manger et al. |
| 7,476,363 | B2 | 1/2009 | Unger et al. |
| 7,526,741 | B2 | 4/2009 | Lee et al. |
| 7,604,965 | B2 | 10/2009 | McBride et al. |
| 7,666,361 | B2 | 2/2010 | McBride et al. |
| 7,678,547 | B2 | 3/2010 | Eyal et al. |
| 7,691,333 | B2 | 4/2010 | McBride et al. |
| 7,749,737 | B2 | 7/2010 | McBride et al. |
| 7,792,345 | B2 | 9/2010 | Taylor et al. |
| 7,815,868 | B1 | 10/2010 | Jones et al. |
| 7,820,427 | B2 | 10/2010 | Unger et al. |
| 7,833,708 | B2 | 11/2010 | Enzelberger et al. |
| 7,837,946 | B2 | 11/2010 | McBride et al. |
| 2002/0142481 | A1 | 10/2002 | Andersson et al. |
| 2004/0087033 | A1 | 5/2004 | Schembri |
| 2004/0115830 | A1 | 6/2004 | Touzov |
| 2004/0180377 | A1 | 9/2004 | Manger et al. |
| 2005/0019898 | A1* | 1/2005 | Adey et al. ................. 435/286.7 |
| 2005/0053952 | A1 | 3/2005 | Hong et al. |
| 2006/0084012 | A1 | 4/2006 | Nuzzo et al. |
| 2006/0172408 | A1 | 8/2006 | Quake et al. |
| 2006/0233674 | A1 | 10/2006 | Nelson |
| 2006/0281183 | A1 | 12/2006 | Sun et al. |
| 2007/0037295 | A1 | 2/2007 | Vangbo et al. |
| 2007/0134807 | A1 | 6/2007 | Bao et al. |
| 2007/0224617 | A1 | 9/2007 | Quake et al. |
| 2007/0248971 | A1 | 10/2007 | Maerkl et al. |
| 2008/0050283 | A1 | 2/2008 | Chou et al. |
| 2008/0075380 | A1 | 3/2008 | Dube et al. |
| 2008/0108063 | A1 | 5/2008 | Lucero et al. |
| 2008/0129736 | A1 | 6/2008 | Sun et al. |
| 2008/0176211 | A1 | 7/2008 | Spence et al. |
| 2008/0223721 | A1 | 9/2008 | Cohen et al. |
| 2008/0230387 | A1 | 9/2008 | McBride et al. |
| 2008/0264863 | A1 | 10/2008 | Quake et al. |
| 2008/0274493 | A1 | 11/2008 | Quake et al. |
| 2008/0281090 | A1 | 11/2008 | Lee et al. |
| 2008/0292504 | A1 | 11/2008 | Goodsaid et al. |
| 2009/0018195 | A1 | 1/2009 | Balagadde |
| 2009/0069194 | A1 | 3/2009 | Ramakrishnan |
| 2009/0142236 | A1 | 6/2009 | Unger et al. |
| 2009/0147918 | A1 | 6/2009 | Fowler et al. |
| 2009/0168066 | A1 | 7/2009 | Hansen et al. |
| 2009/0239308 | A1 | 9/2009 | Dube et al. |
| 2009/0291435 | A1 | 11/2009 | Unger et al. |
| 2010/0104477 | A1 | 4/2010 | Liu et al. |
| 2010/0120018 | A1 | 5/2010 | Quake et al. |
| 2010/0120077 | A1 | 5/2010 | Daridon |
| 2010/0154890 | A1 | 6/2010 | Maerkl et al. |
| 2010/0166608 | A1 | 7/2010 | Quan et al. |
| 2010/0171954 | A1 | 7/2010 | Quake et al. |
| 2010/0183481 | A1 | 7/2010 | Facer et al. |
| 2010/0184202 | A1 | 7/2010 | McBride et al. |
| 2010/0187105 | A1 | 7/2010 | Unger et al. |
| 2010/0196892 | A1 | 8/2010 | Quake et al. |
| 2010/0197522 | A1 | 8/2010 | Liu et al. |
| 2010/0200782 | A1 | 8/2010 | Unger et al. |
| 2010/0230613 | A1 | 9/2010 | Pieprzyk et al. |
| 2010/0263732 | A1 | 10/2010 | Hansen et al. |
| 2010/0263757 | A1 | 10/2010 | Fernandes et al. |
| 2010/0311060 | A1 | 12/2010 | Facer et al. |
| 2010/0320364 | A1 | 12/2010 | Unger et al. |

FOREIGN PATENT DOCUMENTS

| | | | |
|---|---|---|---|
| WO | WO 2007/033385 | A2 | 3/2007 |
| WO | WO 2007/044091 | A2 | 4/2007 |
| WO | WO 2008/043046 | A2 | 4/2008 |
| WO | WO 2009/100449 | A1 | 8/2009 |
| WO | WO 2010/011852 | A1 | 1/2010 |
| WO | WO 2010/017210 | A1 | 2/2010 |
| WO | WO 2010/077618 | A1 | 7/2010 |
| WO | WO 2011/053790 | A2 | 5/2011 |

* cited by examiner

Disposable plastic plate, Tension line side
Disposable plastic plate with tension line
Fig. 20A
Ensure plate adhesion to IHS is secure
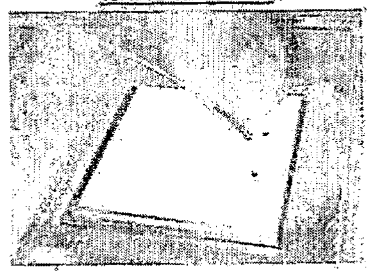
Fig. 20B
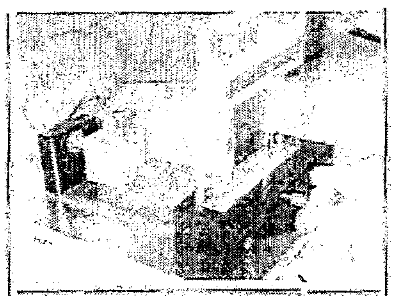
Fig. 20C
Fig. 20D

MICROFLUIDIC DEVICES WITH REMOVABLE COVER AND METHODS OF FABRICATION AND APPLICATION

CROSS-REFERENCES TO RELATED APPLICATIONS

This application is a §371 U.S. national stage entry of International Application No. PCT/SG2010/000369 filed Sep. 9, 2010 and claims the benefit of priority to Singapore Patent Application No. SG 200906624-2 filed Oct. 2, 2009. The content of each of the above filings is incorporated herein by reference.

FIELD OF THE INVENTION

Microfluidic systems are described that include a removable cover as well as methods of recovering samples from these systems. Also described are methods of forming vias in a microfluidic device by detaching a removable cover to from underlying device layers.

BACKGROUND OF THE INVENTION

The ability to perform molecular analyses of chemical and biological systems has grown tremendously in recent years. For example, crystallographic analysis is now available for a variety of molecules, including complex proteins and nucleic acids that were once thought to be uncrystallizable. High-quality crystals of these molecules can be analyzed by x-ray diffraction techniques to produce accurate three-dimensional molecular structures. This 3-D structure information can then be utilized to predict functionality and behavior of the molecule.

However, even today it is still often very difficult to form a high-quality crystal of a complex molecule, requiring a lot of trial and error-not to mention patience and persistence-on the part of the researcher. The large, complex molecular structures of many biological compounds makes them resistant to forming highly ordered crystal structures. Successful crystallization typically requires methodical experimentation with large numbers of reagents and crystallization parameters such as concentration, temperature, solvent type, countersolvent type, and time, among other parameters.

There have also been a lot of advancements in molecular and cellular analysis techniques such as DNA sequencing, gene cloning, monoclonal antibody production, cell transfection, and amplification techniques (such as PCR), among others. Like crystallization, the success of these techniques depends in large measure on the ability to try many possible combinations of samples and reaction environments in hopes of discovering a combination that will permit the analysis.

These "high-throughput" techniques often use densely packed microtiter plates made up of arrays of small volume wells each having a unique combination of reaction conditions (e.g., reagent types, concentrations, etc.). Because the top of the wells are normally left uncovered, control of the reaction environment is limited, and environmental contaminants and fluid evaporation are often a significant problem.

Micro-fluidic pump and valve systems can address the exposure problems by delivering samples and reagents to sealed reaction chambers that are sealed off from the ambient atmosphere. These systems work well carrying out liquid and solution phase reactions in a highly controlled environment. However, when solid-phase products are formed, such as through precipitation or freezing, the micro-fluidic systems can have a difficult time transporting the solids to a point where additional analysis is performed. Ironically, solid samples formed in uncovered microtiter plate wells are easier to access and transport than the solids formed in the micro-fluidic systems. Thus, there is a need for micro-fluidic systems that make it easier to access and transport products from the reaction chambers. This and other problems are addressed by embodiments of the invention.

BRIEF SUMMARY OF THE INVENTION

Microfluidic systems are described having a microfabricated cavity that may be covered with a removable cover, where the removable cover allows at least part of the opening of the microfabricated cavity to be exposed or directly accessed by an operator. The microfluidic systems may include chambers or cavities, flow channels and control channels formed in elastomeric layers that may be made from, for example, PDMS. The removable cover may include a thermoplastic base film bonded to an elastomeric layer (e.g., PDMS) by an adhesive layer. When the removable cover is peeled off, the cavity or chamber may be at least partially exposed to allow direct sample extraction from the chamber. The sample may include solid materials such as precipitated macromolecular crystals and/or a solidified/frozen reaction product that are easily extracted by peeling away at least part of the cover. Methods of making these peelable cover microfluidic systems are also described, including the formation of vias in elastomeric layers by using the removable cover.

More specifically, embodiments may include microfluidic systems that may have a base substrate, and a sample holding layer formed on the base substrate. The sample holding layer may include a microfabricated cavity or recess having an opening formed on a surface of the layer that faces opposite the substrate. The systems may also include a flow channel coupled to the cavity for delivering a reagent to the cavity, and a control channel that intersects the flow channel and forms a deflectable membrane over at least a portion of the intersection. The actuation of the control channel causes deflection of the deflectable membrane to open or close the flow channel. The systems may further include a removable cover bonded to the sample holding layer. The cover is removable to expose at least part of the opening in the microfabricated cavity.

Embodiments may also include methods of microfabricating a microfluidic systems with removable covers. The methods may include the steps of providing a base substrate, and bonding a sample holding layer to the base substrate. The sample holding layer may include a microfabricated cavity or recess having an opening formed on a surface of the layer that faces opposite the substrate. The methods may also include microfabricating a flow channel coupled to the cavity for delivering a reagent to the cavity, and microfabricating a control channel that intersects the flow channel and forms a deflectable membrane to open or close the flow channel. The actuation of the control channel causes deflection of the deflectable membrane to open or close the flow channel. The methods may still further include bonding a removable cover to the sample holding layer for sealing the cavity. The cover is removable to expose at least part of the opening in the microfabricated cavity.

Embodiments may yet further include methods of constructing a via in a peelable cover microfluidic device. The methods may include the steps of microfabricating a mold containing a post, spinning a first elastomeric layer on the mold containing the post to cover the top of the post to a depth, bonding a removable cover to the spinning elastomeric layer, and removing the cover from the post to form a via.

Embodiments may still further include methods for PCR sample extraction from a microfluidic system with a removable cover. The methods may include initiating a polymerase chain reaction (PCR) inside a reaction chamber of the microfluidic system at a first temperature, where the reaction chamber in a first elastomeric layer is covered with a removable cover. The methods may also include placing the microfluidic system with the removable cover in an environment at a second temperature to freeze the reaction chamber, opening the removable cover to expose at least a portion of the reaction chamber, and extracting the frozen PCR sample from the reaction chamber.

Additional embodiments may include a microfluidic device for removing a component. The microfluidic device includes a microfluidic assembly comprising a carrier, a microfluidic chip coupled to the carrier, a removable component attached to the microfluidic chip, an adhesive sheet having a first side and second side, and a cover plate. The first side of the adhesive sheet is bonded to the removable component, while the second side of the adhesive sheet is bonded to the cover plate. Furthermore, the microfluidic device includes a first hooking component coupled to the cover plate and adhesive sheet, and a carrier holder comprising a sidewall and a hollow portion configured to dispose the microfluidic assembly in the hollow portion, where the sidewall is sized such that the removable component can be removed either above the sidewall or through an open portion of the sidewall. Moreover, the microfluidic device includes a slider coupled to the carrier holder, a tension wire coupled to the first hooking component, and a second hooking component coupled to the tension wire, the second hooking component being movable relative to the slider.

Other embodiments include methods for peeling off a removable component. The methods include loading a microfluidic assembly into a holder, where the microfluidic assembly includes a microfluidic carrier, a microfluidic chip coupled to the microfluidic carrier, a removable component attached to the microfluidic chip, an adhesive sheet having a first side and second side, and a cover plate. The first side of the adhesive sheet is bonded to the removable component, the second side of the adhesive sheet is bonded to the cover plate. The holder is sized such that the removable component can be removed from one sidewall of the holder. The methods also include connecting a first hooking component to a second hooking component using a tension wire, where the first hooking component is attached to the removable component through the adhesive sheet and cover plate, the second hooking component is movable relative to a slider attached to the holder. The methods further include applying a tension to the second hooking component and separating the removable component from the microfluidic chip after a time period.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and drawings.

BRIEF DESCRIPTION OF THE DRAWINGS

FIGS. 20*a-d* show photographs of actual device used in Fluidigm.

DETAILED DESCRIPTION OF THE INVENTION

Exemplary peelable cover microfluidic systems, as well as methods of make and using them are described. In addition, exemplary microfluidic vias and methods of making them with peelable covers or layers are also described. The peelable covers may be made from a composite of more than one layer, including a semi-rigid layer, an adhesive layer, and an elastomeric layer that may be closely related or identical to an opposite facing layer on the that has an opening for a microfluidic reaction chamber. Peeling off a portion or all of the removable cover may create an opening in the underlying microfluidic device that permits access to the contents of a reaction chamber. Additional details of the systems and methods are provided below.

Exemplary Peelable Cover Systems

1. System Overview

Figure 1A:
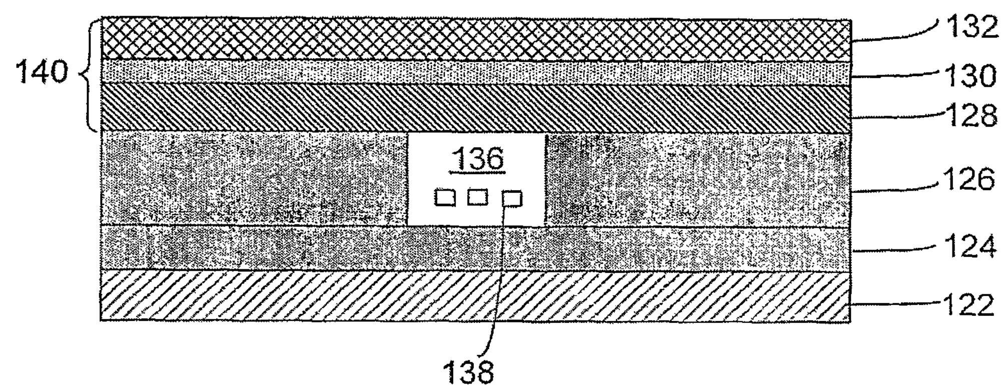
FIG. 1A shows a cross-sectional view of an embodiment of a peelable cover microfluidic system with the cover in an unpeeled state.
Figure 1B:
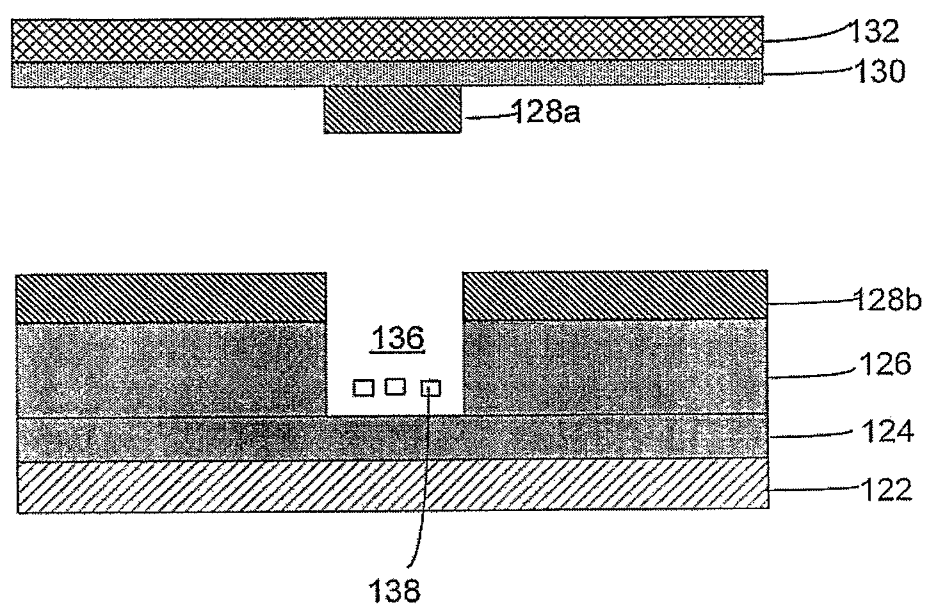
FIG. 1B shows an embodiment of a peelable cover microfluidic system with the cover peeled away from the underlying system components.

FIGS. 1A and 1B show simplified cross-sectional embodiments of a peelable cover microfluidic system where the cover is in an unpeeled (FIG. 1A) and peeled (FIG. 1B) state. In FIG. 1A, the removable cover 140 attached to the underlying system components includes a thermoplastic layer 132 bonded to an elastomer layer 128 by using an adhesive layer 130. The underlying system components may include a pour layer 124 disposed on top of a substrate 122. A spin layer 126 may be formed over the pour layer 124. Layers 124, 126 and 128 may all be made of the same elastomeric material to form the perimeter of chamber 136 from one material. Alternatively, one or more of the these layers 124, 126 and/or 128 may be made from different materials. In an alternative embodiment of the present invention, the pour layer 124 and the spin layer 126 may be replaced by a non-elastomer layer, such as etched glass.

The chamber 136 can hold fluid and solid-phased sample materials including fluid-phased reagents and solvents, and solid-phased reaction products 138. The reaction products 138 may include precipitates from fluid-phased reactants and/or materials that have undergone a phase change due to a temperature change (e.g., freezing). Solid-phase products can include biological materials such as proteins, protein crystals, and nucleic acids, and chemical materials such as polymers or inorganic crystals, among other types of materials.

FIG. 1B shows another embodiment of a peelable cover microfluidic system with the removable cover 140 peeled off the chamber. In the embodiment shown, a portion 128*a* of the elastomer layer 128 overlapping with the opening of the chamber 136 remains adhered to the adhesive layer 130 or the thermoplastic layer 132 of the removable cover 140. Another portion 128*b* of the elastomer layer 128 that does not overlap with the opening of the chamber 136 still remains bonded to the spin layer 126 after the removable cover is peeled off. Peeling off the removable cover exposes the chamber 136 to allow access the chamber 136 and its contents (e.g., reaction products 138).

2. Exemplary Fluid Flow & Control Systems

The solvents, reagents, reactants and/or other fluids shown in chamber 136 may be delivered by fluid flow channels that are also formed in the peelable cover system. Embodiments of the system include features such as channels, valves, vias, and chambers, that are at least partially contained, embedded, or formed by or within one or more layers or levels of an elastomeric block. An exemplary microfluidic device has a reagent flow channel, or reagent line, formed in a first layer of an elastomer. The reagent flow channel includes a containment valve and a chamber conduit. The microfluidic device may also have a control channel, or containment line, formed in a second layer of the elastomer adjacent to the first layer. Further, the microfluidic device may contain a sample flow channel, or sample line, formed in a third layer of the elastomer adjacent to the second layer. The sample flow channel may include a containment valve and a chamber conduit. The control channel can be in operative association with both the reagent flow channel containment valve and the sample flow channel containment valve. A reaction chamber (e.g., chamber 136) may be in fluid communication with the reagent line, and the sample line. At another location, these lines may be in fluid communication with a reagent chamber and a sample chamber. The reaction line may include an interface valve. The microfluidic device may also include an interface channel formed in another layer of elastomer. The interface channel can be in operative association with the reaction flow channel interface valve.

Figure 2:
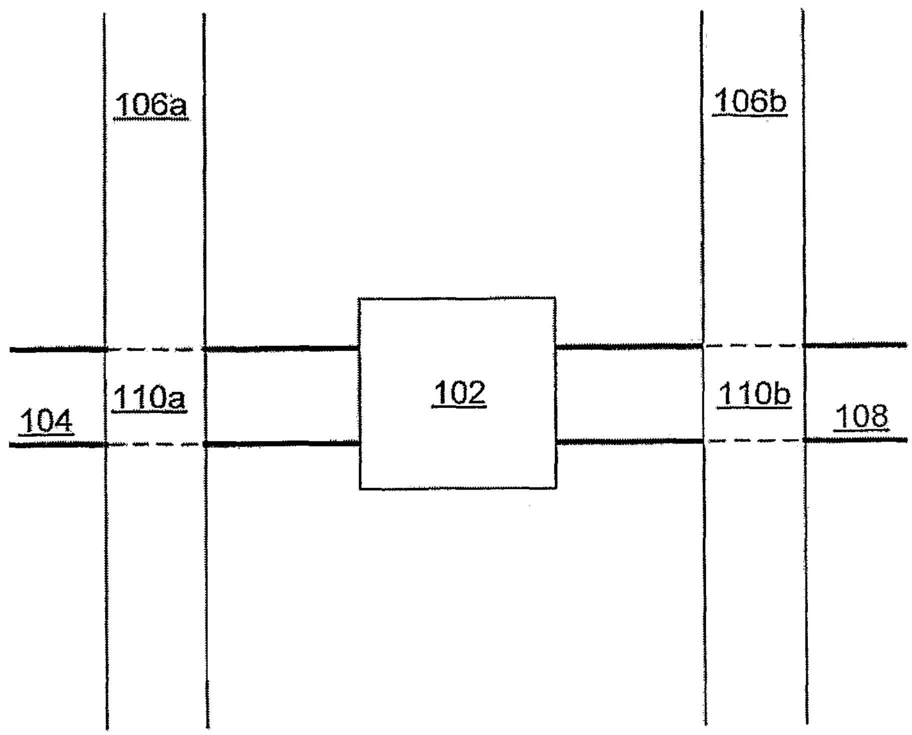
FIG. 2 shows a simplified schematic of microfluidic flow and control lines according to embodiments of the invention.

For example, FIG. 2 shows a simplified schematic of a microfluidic system having a flow channel 104, control channels 106*a-b*, and chamber 102 to transport and react fluid samples. The chamber 102, where reactions may take place to produce solid-phased products, may have a peelable top layer (i.e., cover) that is coplanar with page. The chamber 102 may be in fluid communication with the flow channels 104 and 108. The control channels 106*a-b* have intersections 110*a-b* with the flow channel 104. The intersection areas 110*a-b* of the control channels 106*a-b* or membranes 110*a-b* are deflectable. When the membranes 110*a-b* are deflected, fluid flow is stopped in flow channel 104. The control channels 106*a-b* intersect with the flow channel 104 to form valves for controlling flow on/off in flow channels.

Figure 3:
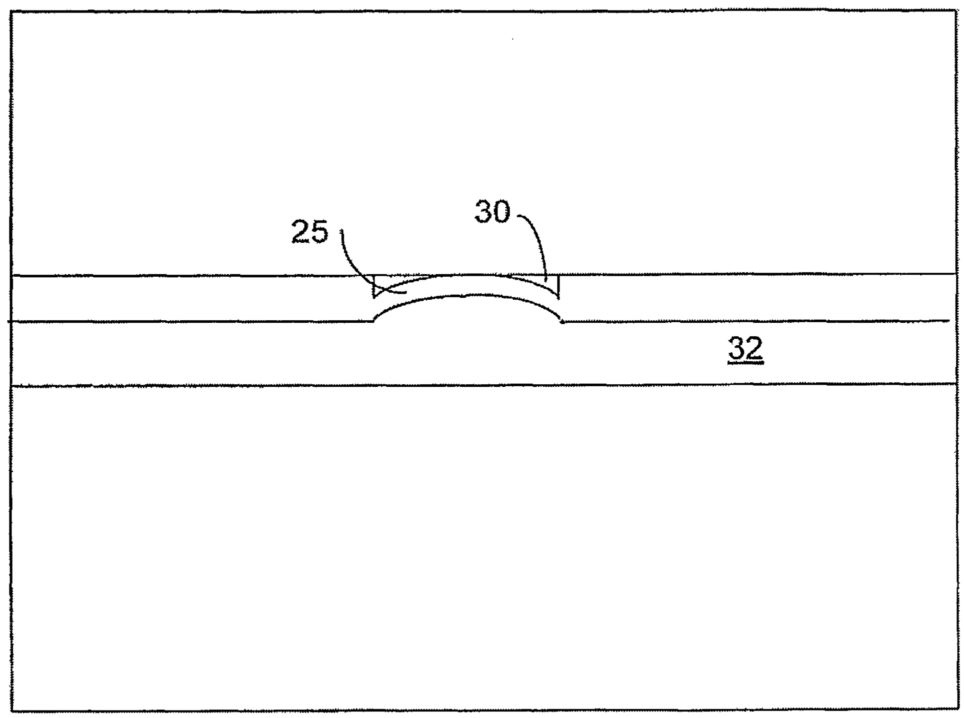
FIG. 3 shows a simplified cross-section of a deflectable membrane being deflected into a flow channel according to embodiments of the invention.

FIG. 3 shows a simplified cross-sectional view of a deflectable membrane 25 in a deflected position. As FIG. 3 shows, pressurization of control channel 32 (either by gas or liquid introduced therein) causes membrane 25 to deflect upward, thereby pinching off the fluid flow passing through flow channel 30. Accordingly, by varying the pressure in channel 32, a linearly actuable valving system is provided such that flow channel 30 can be opened or closed by moving membrane 25 as desired.

In the embodiment shown in FIG. 3, the deflectable membrane 25 is part of the same layer as the flow channel 30. Alternatively, the membrane 25 could be part of the same layer as control channel 32. Also, for illustration purposes here, channel 30 is shown in a "mostly closed" position, rather than a "fully closed" position that would completely cut off fluid flow going in and out of the page of the figure. Additional details of the fluid flow and control lines shown in FIGS. 2 & 3 are described in U.S. patent application Ser. No. 09/605,520, filed Jun. 27, 2000, and titled "Method of Making a Microfabricated Elastomeric Valve," the entire contents of which are herein incorporated by reference for all purposes. Additional embodiments of flow and control line designs in peelable cover microfluidic system are now described.

In preferred aspects, flow channels preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110

μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

Since such valves are actuated by moving the roof of the channels themselves (i.e.: moving membrane) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fL to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

i. Sidewall Coupled Fluid Flow Lines

Figure 4:
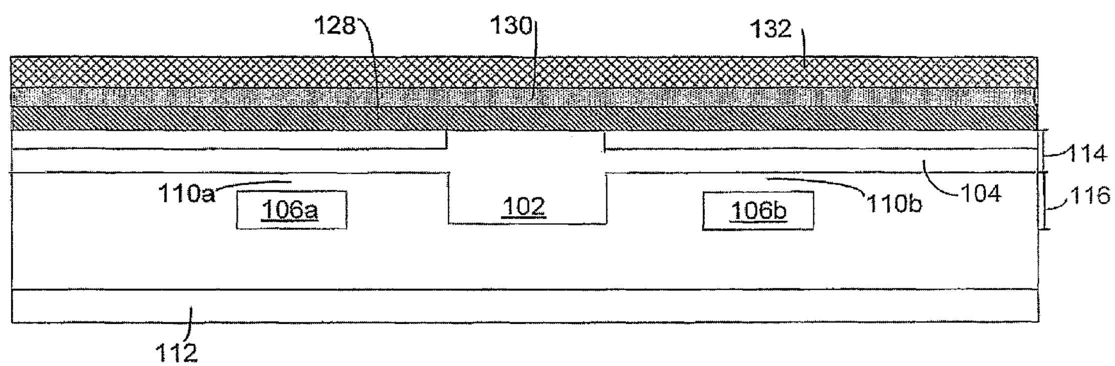
FIG. 4 shows a perspective view of an embodiment of a peelable cover microfluidic system with flow channel coupled to a sidewall of a reaction chamber.

FIG. 4 shows a perspective view of an embodiment of peelable cover microfluidic system where fluid flow channel 104 is fluidly coupled to a sidewall of the chamber 102. The fluid coupling allows fluid flowing through the flow channel 104 to be delivered into the chamber 102. Control channels 106*a-b* are formed in a different elastomer layer 116 than the flow channel 104 in an elastomer layer 114, which is disposed over a substrate 112. The flow of fluids through flow channel 104 is controlled by the actuation of control channels 106*a-b* to deflect one or both of deflectable membranes 110*a-b* into the flow channel 104. The deflectable membranes 110*a-b* may be deflected to a point where fluid flow stops downstream of the membranes, effectively pinching off the flow channel 104. The removable cover comprising 128, 130 and 132 is on top of the flow channel 104.

ii. Via Coupled Fluid Flow Lines

Additional embodiments of peelable cover microfluidic systems may have fluid flow lines that run underneath the chamber holding the solid-phase reaction products. The fluid lines may be fluidly coupled to the chamber with a vertical via formed between the bottom of the chamber and the top of the flow line.

Figure 5:
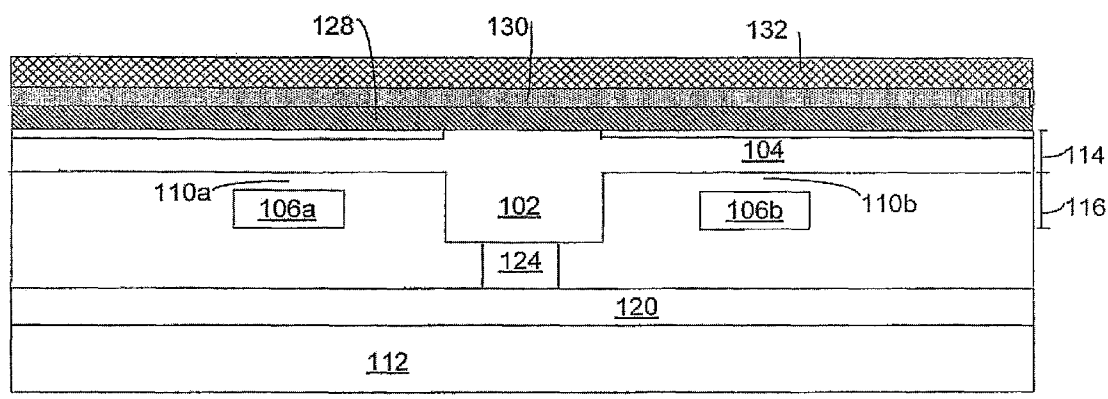
FIG. 5 shows an embodiment of a peelable cover microfluidic system with a flow channel coupled to a reaction chamber through a via.

Referring now to FIG. 5, another flow channel 120 and a via 124 are added to FIG. 4. The via 124 is in a fluid communication with the chamber 102 with the flow channel 120.

Exemplary Methods of Extracting Solid Products From Peelable Cover Systems

Figure 6:
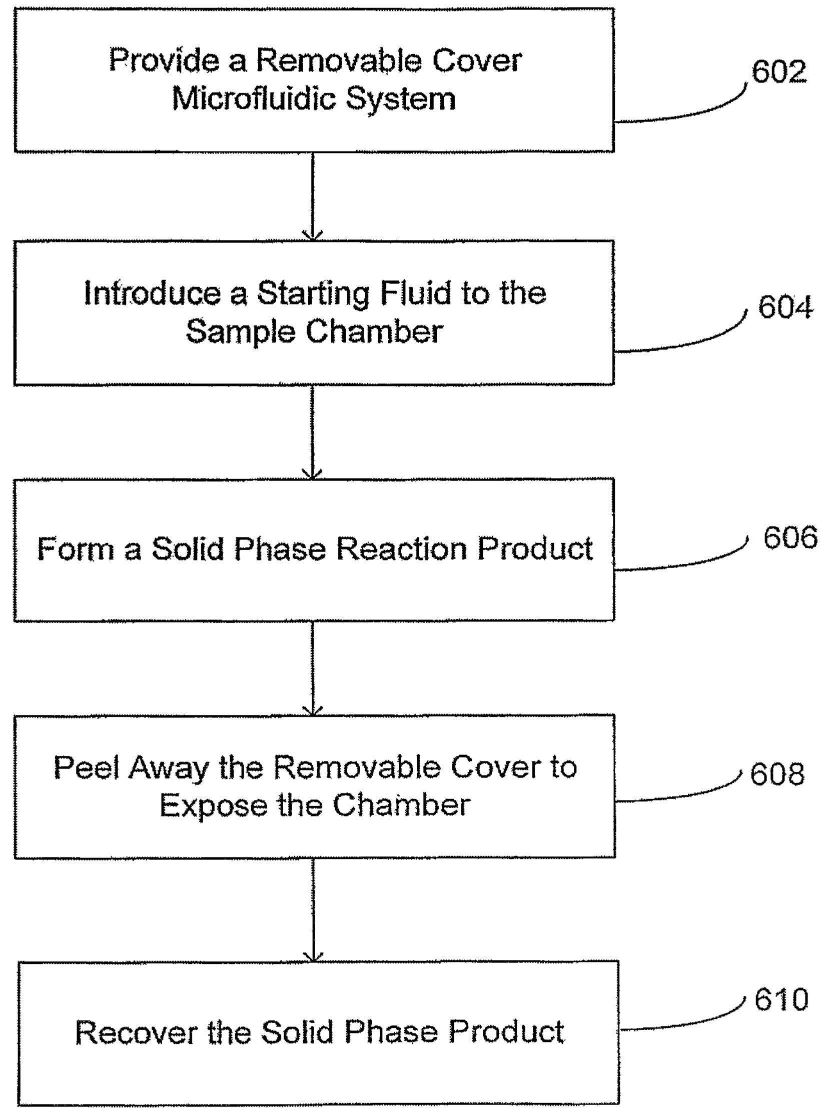
FIG. 6 is a flowchart that includes selected steps in a method of recovering solid materials from a peelable cover microfluidic system according to embodiments of the invention.

FIG. 6 is a flowchart that includes selected steps in a method of recovering solid materials from a peelable cover microfluidic system according to embodiments of the invention. These methods may include providing a peelable cover microfluidic system 602 that includes a sample chamber where solid-phase materials are formed (e.g., solid-phase reaction products). A surface of the sample chamber (e.g., a top side) is at least partially removable (i.e., peelable) to permit unobstructed access to the contents of the chamber.

The methods may also include introducing a starting fluid (e.g., a reactant solution) to the sample chamber 604. This may include introducing one or more fluid streams to the chamber from one or more fluid lines. For example, a sample fluid containing a chemical or biological sample may be introduced through a first fluid line and a reagent solution for crystallization and/or precipitating a portion of the sample may be introduced to the chamber through a second line. As the two fluid streams from the two separate fluid lines are combined in the sample chamber, they may react to form a solid-phase reaction product 606.

The starting fluid(s) may be introduced to the sample chamber by operation of a one or more isolation valves, closing one or more interface valves, and flowing material past the isolation valves and into one or more chambers, optionally under pressure. Transport techniques may also include changing the pressure in a containment line to close the isolation valves, so as to seal off the individual chambers, and changing the pressure in an interface line, so as to open an interface valve. A first material in a first chamber can flow past an open interface valve and into a second chamber, where the first material mixes or reacts with a second material contained therein.

Additional embodiments include performing other steps to four solid-phased reaction products 606. For example, changes in temperature (e.g., increasing or decreasing the temperature of the sample chamber) or light exposure (e.g. UV irradiation) may be performed in addition to (or in lieu of) mixing starting fluids to form solid-phased reaction products. Temperature changes may include lowering the temperature below a freezing point of a liquid (e.g., aqueous) solution in the reaction chamber to solidify substantially all of the contents of the chamber.

The removable cover may be at least partially peeled away to expose at least part of the sample chamber 608. Embodiments include peeling the cover away after solid-phase reaction products have formed, or before they have formed. For example, the cover may be peeled away to expose the fluid contents of the chamber to light or an atmosphere that causes the formation of solid-phase reaction products. The cover may be completely separated and removed from the underlying components including the sample chamber, or partially separated.

Following the peeling back of the cover, the solid-phase materials in the chamber may be recovered 610. Embodiments of the method include the recover of a portion of the solid-phase materials, or substantially all of these materials. The solid-phased materials may also be recovered as a plurality of solid particles or as a single piece. For example, recovery may involve the extraction of a single block of frozen material following the freezing of the sample chamber (see, e.g., the PCR application below). In some embodiments, accessing the solid-phase material through a larger opening in the exposed sample chamber may be the only way to recover the solid products because they are too large to transport through the fluid channels in the system. In addition, avoiding the transport of the solid-phase materials through the fluid channels reduces the chance that the materials will be damaged due to fluid pressure and capillary forces (among other forces).

Figure 7:
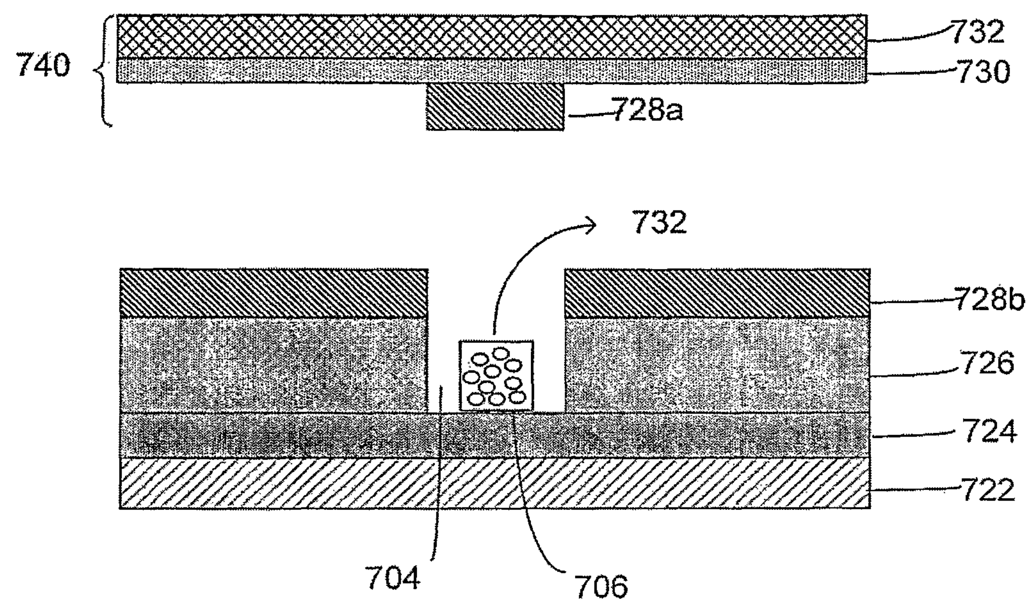
FIG. 7 is a simplified drawing of solid materials being recovered from a peelable microfluidic system according to embodiments of the invention.

FIG. 7 shows cross sectional view of a microfluidic system where a peelable cover 740 has been separated from the rest of the system to expose sample chamber 704, and extraction tool 732 is removing the solid-phase materials 706 from the chamber. The chamber 704 is a cavity in a spin layer 726 that is disposed over a pour layer 724 which is over the top of substrate 722. The removable cover 740 is made from a thermoplastic layer 732 bonded to an elastomer layer 728 by an adhesive layer 730. The removable cover 740 was bonded to the spin layer 726 prior to being peel away. The pour layer 724 and the spin layer 726 are made from the same material as the elastomer layer 728 of the peelable cover 740. In an alternative embodiment of the present invention, the pour layer 724 and the spin layer 726 may be replaced by a non-elastomer layer, such as etched glass.

Exemplary Methods of Making Removable Cover Microfluidic Systems

Figure 8:
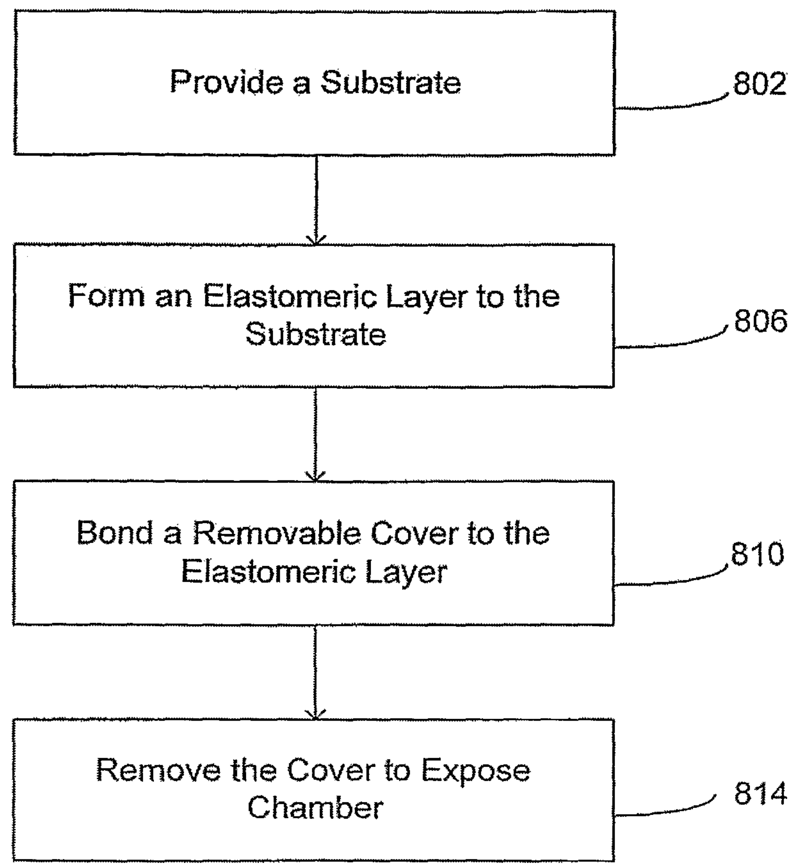
FIG. 8 is a flowchart with selected steps in a method of making a peelable cover microfluidic system according to embodiments of the invention.

FIG. 8 is a flow chart illustrating selected steps in methods of microfabricating a microfluidic system with removable cover according to embodiments of the invention. The methods may include providing a substrate 802 having a raised structure on its surface. The substrate may be a micro-machined mold fabricated by conventional silicon processing methods, including but not limited to photolithography, ion-milling, and electron beam lithography. The machining may create the raised structures on an otherwise planar substrate.

An elastomeric layer may be formed on the substrate 806 with the raised structure forming at least a portion of a sample chamber in the elastomeric layer. This elastomeric layer may be formed by spin coating or pouring an elastomeric material, such as a polysiloxane (e.g., polydimethylsiloxane), on top of the substrate and allowing it to cure into the elastomeric solid.

The substrate may also include structures for flow channels, control channels, fluid reservoirs, and/or other components that may also be formed in the elastomeric layer. Alternatively some or all of these components may be formed in one or more other elastomeric layers. The flow channels may open directly into the sample chamber to provide fluids from a fluid source (e.g., a sample reagent reservoir), and/or they may be fluidly coupled to a via or some other structure that itself has direct fluid access to the sample chamber. The control channels are configured to control the flow of fluids through the flow channels. This control may include attenuating or stopping the flow of fluids from a fluid source to the sample chamber as well as encouraging fluid flow by opening choke points in the flow channel and/or actuating in a concerted fashion to actively pump fluid through flow channels (e.g., peristaltic pumping).

Following the formation of the elastomeric layer 806 a removable (e.g., peelable) cover layer may be formed 808 and bonded to elastomeric layer 810. Embodiments of the cover layer include a outermost layer of semi-rigid plastic, such as a layer of poly(ethylene terephthalate) (PET) glued to an elastomeric layer, such as a polysiloxane, by an adhesive sandwiched between the two layers (e.g., a transparent adhesive such as Optically Clear Laminating Adhesive 8142 from the Minnesota Mining and Manufacturing Co.). The elastomeric layer of the removable cover may be made from the same material as the elastomeric layer formed on the substrate.

The removable cover may be formed apart from the formation of the elastomeric layer 806. For example, forming the cover layer may start by using the semi-rigid plastic layer (or alternatively a glass layer) as a substrate upon which the adhesive layer is applied. A preformed elastomeric layer may then be glued to the semi-rigid plastic layer via the adhesive to form the cover layer. Alternatively, the adhesive layer may be applied to a surface of the elastomeric layer, and then the semi-rigid plastic layer may be glued to the elastomer.

In additional embodiments, layers of the removable cover may be formed or adhered first on the substrate elastomeric layer before the remaining cover layers are glued or otherwise bonded to these cover layers. For example, the cover elastomeric layer may either be formed directly on the substrate elastomeric layer (e.g., pour coated, spin coated, etc.) or preformed and bonded (e.g., plasma bonded) to the substrate elastomeric layer. Afterward, an adhesive may be applied to an exposed surface of the cover elastomeric layer and/or a semi-rigid outermost/topmost layer to glue together these two layers and complete the formation of the removable cover.

As noted above, plasma bonding (or some other type of bonding) may be used to bind the elastomeric layer of the cover to the elastomeric layer on the substrate 810. However, this elastomer-elastomer bonding does not occur where the top side structure for the sample chamber has displaced the elastomer formed on the substrate. Thus, the bonding interface between these layers include areas where very little or no bonding occurs. In these areas, the adhesive bonding between the upper layer of semi-rigid plastic and the upper elastomer layer is stronger than the bond formed between that elastomer layer and the underlying elastomer layer formed on the substrate.

When the removable cover is removed 814 (e.g., peeled off) of the underlying elastomeric structure, the portions of the cover's elastomeric layer bonded to the underlying substrate elastomer layer will stay bonded, and instead separate from the adhesive layer of the cover. On the other hand, for those areas where the structure in the substrate elastomer layer displaced elastomer to elastomer bonding, the cover's elastomeric layer stays glued to the adhesive layer, and gets peeled away with the cover. As a result, removing the cover 814 exposes the top of the sample chamber while keeping the sidewalls and bottom of the chamber undisturbed. The exposure provides easy access and recovery of the contents of the sample chamber without having to transport then through microfluidic channels that could damage or destroy sample products such as macromolecular crystals and complex biomolecules (e.g., proteins and nucleic acids).

Given the tremendous diversity of polymer chemistries, precursors, synthetic methods, reaction conditions, and potential additives, there are a huge number of possible elastomer systems that could be used to make elastomeric blocks, layers, membranes, microvalves, pumps, and the like. Variations in the materials used may in some cases be driven by the need for particular material properties, e.g., solvent resistance, stiffness, gas permeability, or temperature stability. There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones or polysiloxanes.

Polyisoprene, polybutadiene, and polychloroprene are all polymerized from diene monomers, and therefore have one double bond per monomer when polymerized. This double bond allows the polymers to be converted to elastomers by vulcanization (generally, sulfur is used to form crosslinks between the double bonds by heating). This would easily allow homogeneous multilayer soft lithography by incomplete vulcanization of the layers to be bonded; photoresist encapsulation would be possible by a similar mechanism.

Pure polyisobutylene has no double bonds, but is crosslinked to use as an elastomer by including a small amount (about 1%) of isoprene in the polymerization. The isoprene monomers give pendant double bonds on the polyisobutylene backbone, which may then be vulcanized as above.

Poly(styrene-butadiene-styrene) is produced by living anionic polymerization (that is, there is no natural chain-terminating step in the reaction), so "live" polymer ends can exist in the cured polymer. This makes it a natural candidate for a photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes are produced from di-isocyanates (A--A) and di-alcohols or di-amines (B--B); since there are a large variety of di-isocyanates and di-alcohols/amines, the number of different types of polyurethanes is huge. The A vs. B nature of the polymers, however, make them useful for heterogeneous multilayer soft lithography just as RTV 615 is: by using excess A--A in one layer and excess B--B in the other layer.

Silicone polymers have great structural variety, and provide a great number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

In addition to the use of the simple "pure" polymers discussed above, crosslinking agents may be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

The following is a non-exclusive list of elastomeric materials which may be utilized in connection with the present invention: polyisoprene, polybutadiene, polychloroprene, polyisobutylene, poly(styrene-butadiene-styrene), the polyurethanes, and silicone polymers; or poly(bis(fluoroaLkoxy) phosphazene) (PNF, Eypel-F), poly(carborane-siloxanes) (Dexsil), poly(acrylonitrile-butadiene) (nitrile rubber), poly (l-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

Allcock et al, Contemporary Polymer Chemistry, 2nd Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Materials having a Young's modulus of between about 1 Pa to about 1 TPa, or between about 10 Pa to about 100 GPa, or between about 20 Pa to about 1 GPa, or between about 50 Pa to about 10 MPa, or between about 100 Pa to about 1 MPa are useful in accordance with embodiments of the present invention, although materials having a Young's modulus outside of these ranges could also be utilized depending upon the needs of a particular application. In some cases, materials can have a Young's modulus of about 100 MPA (megapascals) or less. In other embodiments, the Young's modulus of the material is about 75 MPA or less, about 50 MPa or less, about 25 MPa or less, about 10 MPa or less, about 8 MPa or less, about 5 MPa or less, or about 2 MPa or less.

The elastomer may comprise a silicon rubber such as RTV 615 in the present invention, but not limited to. RTV 615 is transparent to visible light and is also bio-compatible such that it is suitable for applications in microbiology. The substrate 122 may comprise a glass. An advantage of using glass as substrate is that the elastomeric structure may be peeled up, washed, and reused. A further benefit of using glass is that optical sensing may be employed. Alternatively, the substrate may be an elastomer itself, especially in a situation when higher back pressures are required.

Several bonding methods may be used, such as heating, plasma bonding, bonding by using an uncured elastomer etc. In the present invention, the elastomer layer comprises RTV 615, although other elastomers may be used. Several possible bonding methods for the elastomer R615 are discussed here. RTV 615 silicone is a two-part addition-cure silicon rubber. Part A contains vinyl groups and catalyst; part B contains silicon hydride (Si—H) groups. The conventional ratio for RTV 615 is 10A:1B. The ratio for RTV 615 also includes 1A:1B. For bonding, one layer may be made with 30A:1B (i.e. excess vinyl groups) and the other with 3A:1B (excess Si—H groups). Each layer is cured separately. When the two layers are brought into contact and heated at elevated temperature, the two layers bond irreversibly forming a monolithic elastomeric substrate.

Alternatively, other bonding methods may be used, including activating the elastomer surface by plasma exposure, so that the elastomer layers/substrate will bond when placed in contact. One approach to bonding two elastomer layers of the same material is set forth by Duffy et al, "Rapid Prototyping of Microfluidic Systems in Poly(dimethylsiloxane) (PDMS)", Analytical Chemistry (1998), 70, 4974-4984, incorporated herein by reference for all purposes. This paper discusses that exposing PDMS layers to oxygen plasma causes oxidation of the surface, with irreversible bonding occurring when the two oxidized layers are placed into contact.

Yet, another approach to bonding together successive layers of elastomer is to utilize uncured elastomer. Specifically, a thin layer of uncured elastomer such as RTV 615 is applied on top of a first cured elastomeric layer. Next, a second uncured elastomeric layer is placed on top of the uncured elastomer. The thin middle layer of uncured is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again result in formation of a monolithic elastomeric structure.

Exemplary Methods of Making Vias

Vias may be used to transport fluids vertically between layers (or within a layer) of a microfluidic device. For example, when a flow channel is positioned under a reaction chamber, reagent reservoir, etc., a via positioned vertically between these elements may be used to fluidly connect them. As described below, vertical vias or interconnects between elastomer layers may be fabricated by several methods.

1. Chemical Etching and Laser Ablation

Vertical vias or interconnects may be formed by chemically etching or laser ablating (e.g., laser punching) the via in a substrate block (e.g., a block of elastomeric material). For example, a vertical via in an elastomer layer can be created by etching a hole down onto a raised line or a post on a micromachined mold, and bonding the next layer such that a channel passes over that hole. Specifically, an etch resistant layer is formed on top of an elastomer layer, and a mask with lithographical pattern is formed on top of the etch resistant layer such that the unmasked region can be etched away and mask region is protected by a photoresist layer during etching. Next, the elastomer layer is etched away and the etch resistant layer or etch stop layer is finally removed before adding the next elastomer layer. The chemical etching method for making vias is described in U.S. Pat. No. 6,793,753, the entire content of which is incorporated herein by reference for all purposes. The vias may also be created by using laser cutting.

2. Molding and Peeling

Figure 9:
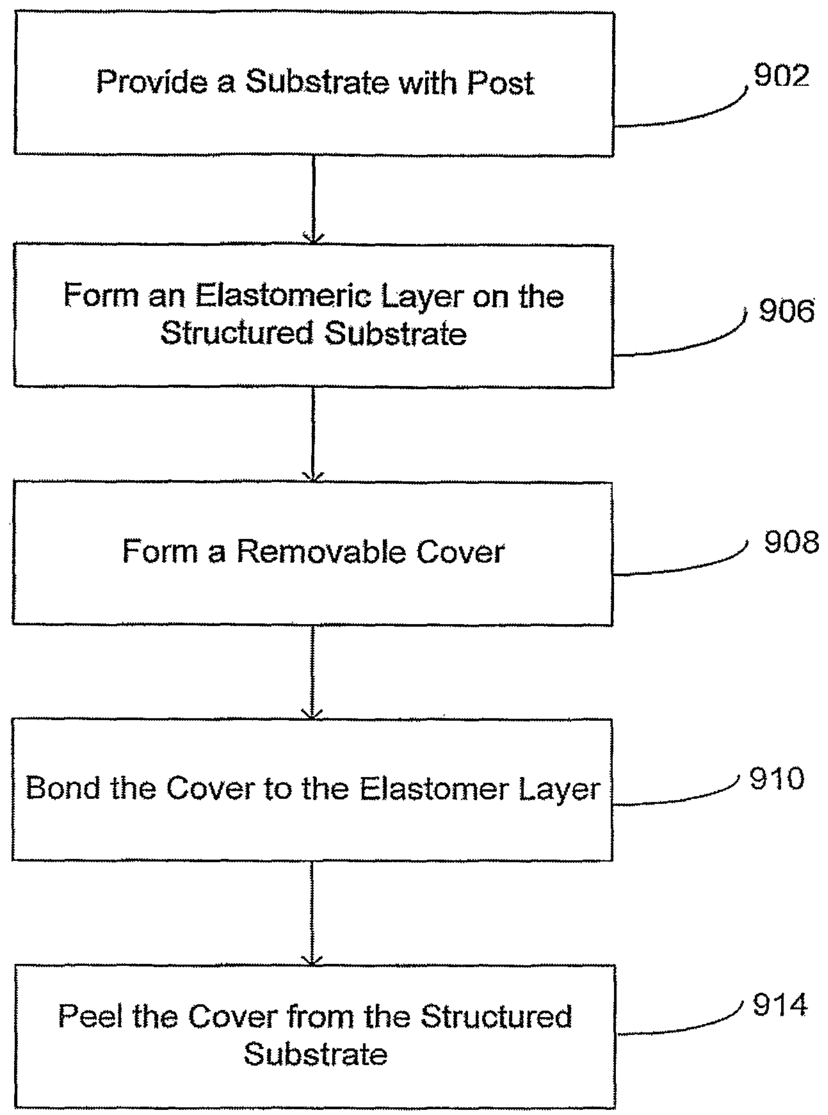
FIG. 9 is a flowchart with selected steps in a method of making a via according to embodiments of the invention.

Methods of forming and exposing microfluidic sample chambers that have removable covers can also be adapted for via formation. FIG. 9 is a flow chart illustrating selected steps in processes that use a removable cover to help form vias in microfluidic devices. The methods may include providing a substrate 902, which may include one or more posts extending from the substantially planar surface of the substrate. The posts may have positions and radii on the substrate to form at least a portion of the vias in the microfluidic device. The substrate may be a micro-machined mold fabricated by conventional silicon processing methods, including but not limited to photolithography, ion-milling, and electron beam lithography. The machining may create the posts and other structures on the planar substrate.

A layer of elastomeric material may be provided on the structured substrate 906. The elastomeric material may be pour coated, spin coated, casted, injected, etc., on the substrate until a desired depth of the material is reached. This depth may be reached when the material has risen to a predetermined level relative to the post. For example, an amount of elastomeric material may be provided that reaches a point below a top surface of the post, at the top surface of the post, or above the top surface of the post (e.g., covering the post to a depth of about 1 μm to about 2 μm). The elastomeric material may then be cured to form a solid elastomeric layer.

An elastomeric material may be selected that has a particular degree of binding (i.e., stickiness) to the underlying substrate mold. For example, a low energy liquid like PDMS may be provided to a mold made of a high energy material such as Teflon, PDMS coated in chemras, perfluoropolyethers, etc., that has a low degree of binding with the PDMS liquid precursor. Thus, very little if any of the PDMS liquid would coat the tops of the mold posts. This allows the elastomeric material to be spin coated or otherwise provided to the mold without forming a residual coating layer on the exposed structural features of the mold.

Following the formation of the elastomeric layer 906 a removable (e.g., peelable) cover layer may be formed 908 and bonded to the elastomeric layer 910. Embodiments of the cover layer include a outermost layer of semi-rigid plastic, such as a layer of poly(ethylene terephthalate) (PET) glued to an elastomeric layer, such as a polysiloxane, by an adhesive sandwiched between the two layers (e.g., a transparent adhesive such as Optically Clear Laminating Adhesive 8142 from the Minnesota Mining and Manufacturing Co.). The elastomeric layer of the removable cover may be made from the same material as the elastomeric layer formed on the structured substrate.

Plasma bonding (or some other type of bonding) may be used to bind the elastomeric layer of the cover to the elastomeric layer on the structured substrate 910. Similar to the removable cover microfluidic sample chamber above, the bonding between elastomer layer is weak or absent where the posts have displaced the elastomer layer formed on the structured substrate. For these areas, the adhesive bonding between the upper layer of semi-rigid plastic and the cover's elastomer layer is stronger than the bond formed between that elastomer layer and the underlying elastomer layer formed on the substrate.

When the removable cover is peeled from the underlying elastomeric layer on the structured substrate 914, the cover's elastomeric layer remains bonded to the underlying elastomeric layer except over the tops of the posts. In those areas, the adhesive bonding to the cover is stronger and can even pull a thin film of the underlying elastomer along with that portion of the cover's elastomeric layer. The resulting elastomeric layer that remains on the posts is a combination of the original elastomeric layer on formed on the structured substrate and the elastomeric layer left behind from the removable cover. This resulting layer includes the openings centered over the posts that define a top part of the vias. When is layer is removed from the structured substrate it will have vias with a depth that is the sum of the thickness of the original elastomeric layer formed on the structured substrate plus the thickness of the cover's elastomeric layer that was left behind.

In some instances, the opening formed after peeling away the removable cover will be rough and not precisely conform to the shape defined by the sidewall surfaces of the posts. A portion of the top surface of may be etched, polished or otherwise removed to a point were there is improved surface uniformity at the ends of the vias.

Exemplary Via Structure

Figure 10A:
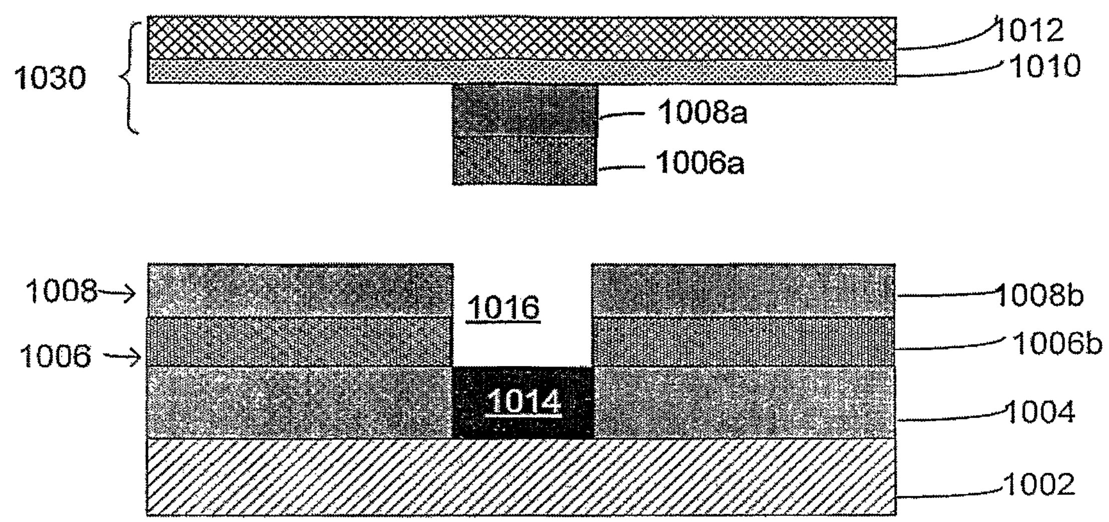
FIG. 10A is a perspective view of an array of vias formed on a micromachined mold according to embodiments of the invention.

FIG. 10A shows that the removable cover 1030 peels off the portion 1006*a* of the spin layer 1006 and the portion 1008*a* of the elastomer layer 1008 of the removable cover 1030 to form a via 1016. The portions 1008*a* and 1006*a* overlap with the top of the post 1014. The portion 1008*b* of the elastomer layer 1008 of the removable cover 1030 that does not overlap with the post 1014 remains bonded to the portion 1006*b* of the spin layer 1006 that does not overlap with the post 1014. The portion 1006*b* remains bonded to the pour elastomer layer 1004. The final via feature in the PDMS has the height of the entire spin layer 1006 plus the thickness of the PDMS layer 1008.

It should be mentioned here that the edges of the portions 1008*b* and 1006*b* may not be substantially like the straight cutting edge as shown in FIG. 10A. The cleanliness of the edge cut may depend upon the sizes of vias, the thickness of the spin layer 1006, the aspect ratio of the post 1014, such as ratio of the diameter of the post 1014 over the depth of the post 1014, the aspect ratio of the thickness of the spin/membrane layer 1006 over the depth of the post 1014. These parameters may be optimized to approach the clean cut of the edges of the vias shown.

Figure 10B:
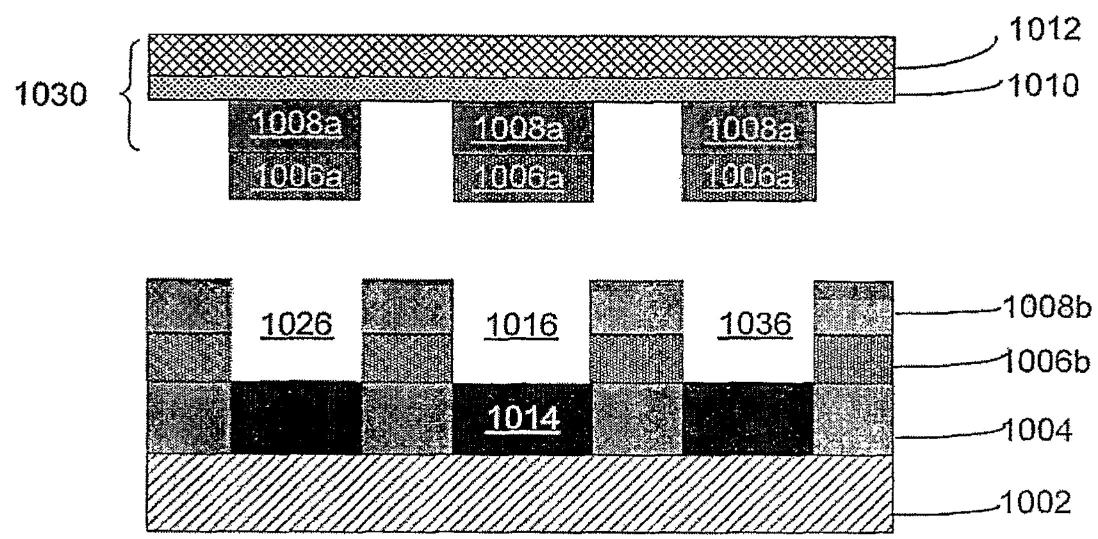
FIG. 10B shows an elastomeric layer containing an array of vias separated from a peeled top layer and underlying micromachined mold according to embodiments of the invention.

FIG. 10B shows an array of vias formed by peeling the removable cover 1030 off the portion 1006*a* of the spin layer and the portion 1008*a* of the elastomer layer 1008 of the removable cover 1030 to form an array of vias 1016, 1026, 1036.

Exemplary Applications of Peelable Cover Systems

Embodiments may also include systems and methods for conducting one or more reactions at one or more selected temperatures or ranges of temperatures over time. These reactions may include nucleic acid amplification reactions (e.g., polymerase chain reactions (PCR)). They may also include crystal forming reactions to grow crystals. The microfluidic systems may include one or more reaction chambers formed in a multi-layer elastomeric block having a peelable cover. The systems may also include a thermal transfer device proximal to or near at least one of the reaction chambers. Reagents for carrying out a desired reaction can be introduced into a microfluidic array device or matrix. Following the reaction, the peelable cover may be partially or completely removed to expose the contents of a reaction chamber and provide access for tools to analyze and/or extract materials from the chamber.

1. Nucleic Acid Amplification Reactions

The device described herein is useful for nucleic acid amplification reactions, including thermal and isothermal nucleic acid amplification reactions such as exponential amplification, linked linear amplification, ligation-based amplification, and transcription-based amplification.

The most commonly used target amplification method is PCR, which is based on multiple cycles of denaturation, hybridization of two oligonucleotide primers, each to opposite strand of the target strands, and primer extension by a nucleotide polymerase to produce multiple double stranded copies of the target sequence. See, for example, Mullis et al. Cold Spring Harbor Symp. Quant. Biol. 51:263-273 (1986); U.S. Pat. Nos. 4,582,788 and 4,683,194. Many variations of PCR have been described, and the method is being used for amplification of DNA or RNA nucleic acid sequences, sequencing, mutation analysis and others. PCR-type nucleic acid amplification reactions are described in some detail below.

Thermocycling-based methods that employ a single primer, have also been described. See, for example, U.S. Pat. Nos. 5,508,178; 5,595,891; 5,683,879; 5,130,238; and 5,679,512. The primer can be a DNA/RNA chimeric primer, as disclosed in U.S. Pat. No. 5,744,308. Other methods that are dependent on thermal cycling are the ligase chain reaction (LCR) and the related repair chain reaction (RCR). The ligase chain reaction is described in EP Application No. 0320308B1. Another example of ligation-based amplification is the ligation amplification reaction (LAR), disclosed by Wu et al. in Genomic 4:560 (1989).

Linked linear amplification is disclosed by Wallace et al. in U.S. Pat. No. 6,027,923. Various methods of transcription-based amplification are disclosed in U.S. Pat. Nos. 5,766,849 and 5,654,142.

Isothermal methods such as strand displacement amplification (SDA) are disclosed by Fraiser et al. in U.S. Pat. No. 5,648,211; Cleuziat et al. in U.S. Pat. No. 5,824,517; Walker et al. Proc. Natl. Acad. Sci. U.S.A. 89:392-396 (1992), and Van Ness et al. in U.S. Patent Publication 20030138800. Other isothermal target amplification methods are the transcription-based amplification methods, in which an RNA polymerase promoter sequence is incorporated into primer extension products at an early stage of the amplification (WO 89/01050), and further target sequence, or target complementary sequence, is amplified by transcription steps and digestion of an RNA strand in a DNA/RNA hybrid intermediate product. See, for example, U.S. Pat. Nos. 5,169,766 and 4,786,600. These methods include transcription mediated amplification (TMA), self-sustained sequence replication (3SR), Nucleic Acid Sequence Based Amplification (NASBA), loop-mediated isothermal amplification (LOOP), and variations there of. See, for example, Guatelli et al. Proc. Natl. Acad. Sci. U.S.A. 87:1874-1878 (1990); U.S. Pat. No. 5,766,849 (TMA); U.S. Pat. No. 5,654,142 (NASBA), Notomi et al. 28(12): Nuc. Acid. Res. e63 (2000) (LOOP), and Guatelli et al. Proc. Natl. Acad. Sci. U.S.A. 87:1874 (1990) (3SR). Other amplifications methods use template switching oligonucleotides (TSOs) and blocking oligonucleotides. For example, the template switch amplification in which chimeric DNA primer are utilized is disclosed in U.S. Pat. No. 5,679,512 and by Patel et al. Proc. Natl. Acad. Sci. U.S.A. 93:2969-2974 (1996) and blocking oligonucleotides are disclosed by Laney et al. in U.S. Pat. No. 5,679,512. Each of the foregoing references are incorporated herein by reference in their entirety for all purposes.

2. PCR-Type Nucleic Acid Amplification Reactions

Figure 11A:
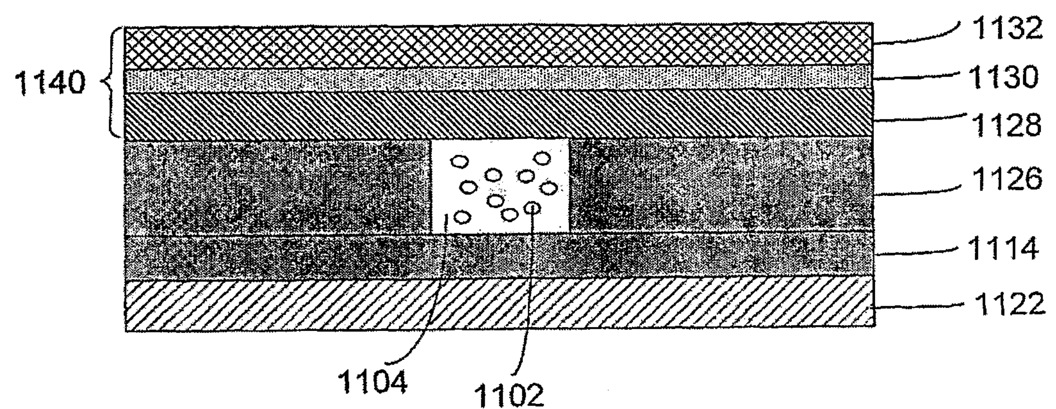
FIGS. 11A & B show cross-sectional views of a peelable cover system that includes a PCR reaction chamber according to embodiments of the invention.

Embodiments of the invention include the use of a peelable cover microfluidic systems in conjunction with polymerase chain reaction (PCR) applications. Peelable cover systems may be used to expose and extract PCR sample products that are too reactive and/or delicate to be extracted through the internal sample or flow channels of a microfluidic system. FIG. 11A shows a cross sectional view of an embodiment of a peelable cover system that includes a PCR reaction chamber. The system is designed to operate at the elevated temperatures that are typical during PCR reaction processes. It may include chamber 1104 to hold the PCR reactants 1102. The chamber 1104 may be formed as a cavity in a spin layer 1126 disposed over a pour layer 1124, which is over the top of substrate 1122. The system may also include a removable cover 1140 having a thermoplastic layer 1132 bonded to an elastomer layer 1128 by an adhesive layer 1130. The removable cover 1140 may be bonded to the spin layer 1126. The pour layer 1124 and the spin layer 1126 may be made from the same material as the elastomer layer 1128 of the peelable cover 1140.

The system may include a thermal transfer device (not shown) proximal to or near the PCR reaction chamber 1104 for setting the chamber 1104 to an elevated temperature at which the PCR reactions to occur. The thermal transfer device can be formed to contact a thermal control source. The system may be contacted with the thermal control device such that the thermal control device is in thermal communication with the thermal control source so that a temperature of the PCR reaction in chamber 1104 is changed or controlled as a result of a change in temperature of the thermal control source. Exemplary thermal cycling techniques are discussed in U.S. Patent Publication No. 2007/0196912, the content of which is incorporated herein by reference. In some embodiments, the microfluidic system may be coupled with or in operative association with an Integrated Heat Spreader (IHS). Such heating mechanisms are discussed in U.S. Pat. No. 7,307,802, the content of which is incorporated herein by reference.

Figure 11B:
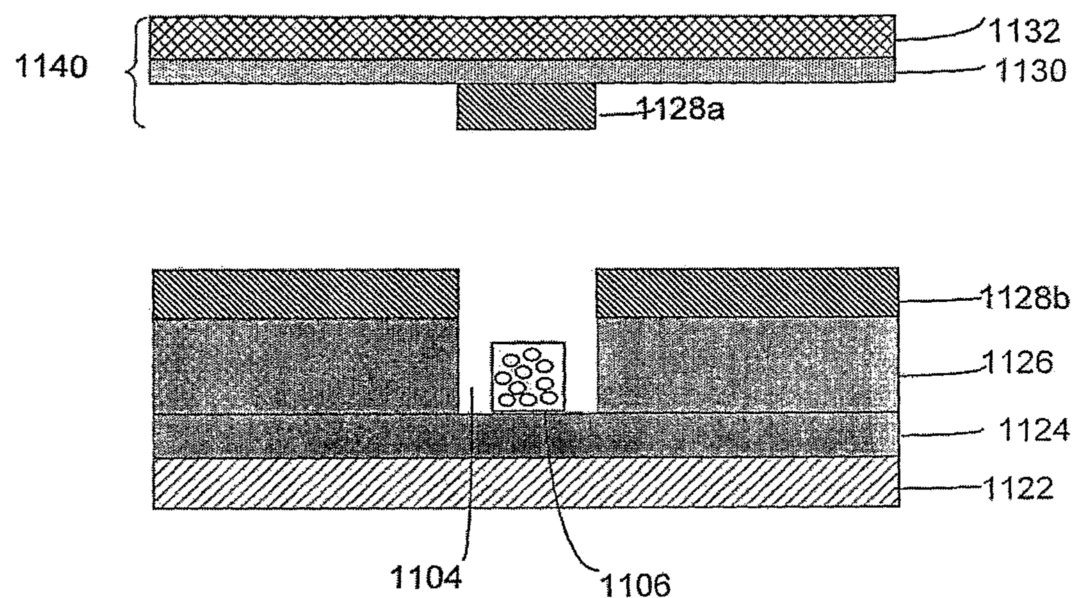

After the PCR reactions have occurred in the reaction chamber 1104, the temperature of the chamber 1104 may be lowered to a point where the solution of PCR reaction products are frozen solid. In some embodiments, the lowering the temperature by be done by contacting the chamber with liquid nitrogen. After the liquid solution has been frozen, the removable cover 1140 may be peeled back or completely separated to expose the frozen block 1106 of PCR reaction products in the reaction chamber 1104. The frozen block 1106 is easily removed from the system once the removable cover 1140 has been peeled back, as illustrated in FIG. 11B.

Figure 12:
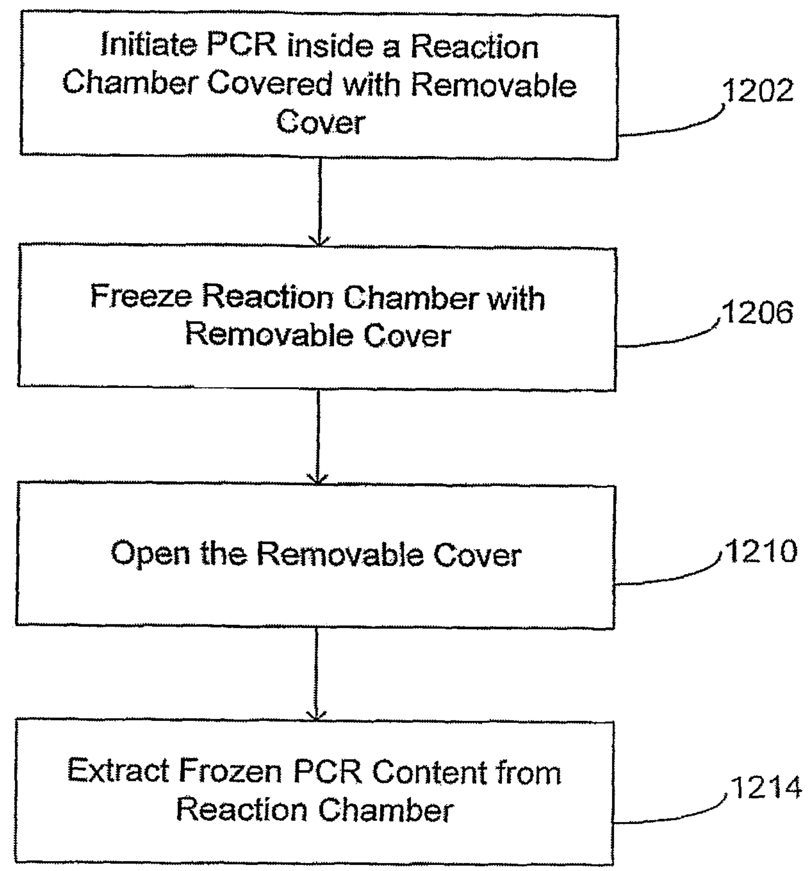
FIG. 12 shows selected steps in a method of forming and recovering PCR reaction products from a peelable cover microfluidic system according to embodiments of the invention.

FIG. 12 is a flow chart summarizing selected steps in a process of creating and removing PCR reaction products from a peelable cover microfluidic system according to embodiments of the invention. The process may include initiating a reaction inside the PCR reaction chamber that is covered with a removable cover 1202. The initiation process may include raising the temperature of the reaction chamber to achieve reasonable reaction rate. Alternatively, the system may be kept at ambient temperature if the PCR reactions can proceed at a reasonable rate without heating the reaction chamber.

After the PCR reaction products are formed, the reaction chamber may be placed into a cold environment such as liquid nitrogen to freeze them 1206 into a frozen block in the reaction chamber. The removable cover may be peeled off the chamber to expose the frozen block and allow it to be inspected and/or extracted from the PCR chamber 1210. The frozen block containing resulting content may be manually taken out by an operator 1214. This method allows the material to be extracted from the PCR chamber by using a tweezer.

The term "PCR," as used herein, generally refers to a method for amplifying, detecting, or quantifying a specific region of an analyte. One skilled in the art appreciates that there are several variations on the basic PCR technique such as allele-specific PCR, assembly PCR or polymerase cycling assembly (PCA), colony PCR, helicase-dependent amplification, hot start PCR, intersequence-specific (ISSR) PCR, inverse PCR, ligation-mediated PCR, methylation-specific PCR, multiplex ligation dependent probe amplification, multiplex PCR, nested PCR, overlap-extension PCR, quantitative PCR, quantitative real-time PCR, RT-PCR, thermal asymmetric interlaces (TAIL) PCR, touchdown PCR, and PAN-AC. Additionally, one skilled in the art would understand how to practice these variations on the basic PCR technique.

Embodiments of the invention may be used to combine the features of a high throughput microfluidic device, labeled nucleic acid probes, and homogenous assays to detect and/or quantify nucleic acid analytes with high PCR and probe specificity. Certain methods described herein may allow for the detection of low copy number nucleic acid analyte per cell, have low fluorescence background yielding a high signal to noise ratio. The homogeneous assays of the invention may have a dynamic range of at least about 3 orders of magnitude, more often at least about 4, even more often at least about 5, even more often at least about 6, often at least about 7, and sometimes at least about 8 orders of magnitude.

According to an embodiment of the invention, the detection and/or quantification of a plurality of nucleic acid analytes from a sample may generally be carried out by obtaining a pre-amplified sample, aliquoting the sample and distributing the pre-amplified sample into reaction chambers of a microfluidic device containing the appropriate buffers, primers, probes and enzymes, performing a homogenous assay for the target nucleic analytes of interest, and querying the aliquots for the presence of nucleic acid analytes.

In one embodiment, a sample is obtained which is suspected of containing the target nucleic acid analyte of interest. The sample may be first reversed transcribed into cDNA and subjected to a preliminary amplification reaction to generate a pre-amplified sample. In the preliminary amplification reaction, the reverse transcribed sample is subjected to 14 cycles of PCR in order to increase the nucleic acid analytes by about 16,000 fold.

In another embodiment, aliquots of the pre-amplified sample are distributed into separated compartments of a microfluidic device and combined with the appropriate reagents. In particular, the aliquot may have a volume of in the range of about 1 picoliter to about 500 nanoliters, more often in the range of about 100 picoliters to about 20 nanoliters, even more often in the range of about 1 nanoliter to about 20 nanoliters, and most often in the range of about 5 nanoliters to about 15 nanoliters. The reagents may include a labeled nucleic acid probe, PCR primers (e.g., forward primers and reverse primers), a thermostable DNA polymerase, GT buffer, an aqueous buffer, magnesium chloride and deoxynucleotide truphosphates, and may also include other non-reactive ingredients. In a specific aspect, a pre-sample mix may be prepared which may include TaqMan Universal PCR master Mix, AmpliTaq-Gold (about 5 units/μl), 20×GT buffer, and $H_2O$. The pre-sample mix may be combined with the nucleic acid of interest, and appropriate primers.

In one aspect, a 1×GT buffer may contain between in a range of about 0.1 M to about 0.8 M, BSA in a range of about 1 mg/ml to about 4 mg/ml, glycerol in a range of about 1% to about 5%, PEG 20,000 in a range of about 1% to about 5%, PEG MME550 in a range of about 0.05% to about 5%, MME5000 in a range of 1% about to about 5%, Superblock® in PBS in a range of about 1% to about 15%, Superblock® T20 in a range of about 1% to about 10%, and Tween 20 in a range of 0.1% about to about 3%. In a specific aspect, the 1×GT buffer may contain about 0.4 M betaine, 2 mg/ml BSA, about 2.5% glycerol, about 2% PEG 20,000, about 1% PEG MME550, about 2.5% MME5000, about 10% Superblock® in PBS, about 5% Superblock® T20, and about 0.5% Tween 20. In a more specific embodiment, the 1×GT buffer may contain about 0.4 M betaine, 4 mg/ml BSA, about 5% glycerol, about 2%

PEG 20,000, about 1% PEG MME550, about 2.5% MME5000, about 10% Superblock® in PBS, about 10% Superblock® T20, and about 1% Tween 20.

In another aspect, a 20×GT buffer may be prepared and may be diluted to a final concentration of 1× when used in the dynamic arrays. For example, a 20×GT buffer may include betaine in a range of about 1M to about 10M, BSA in a range of about 5 mg/ml to about 15 mg/ml, and Superblock® T20 (in TBS) in a range of about 20% to about 65%. In a particular aspect, the GT buffer may include about 5 M betaine, about 10 mg/ml BSA, and about 57% Superblock®T20 in TBS. As one skilled in the art appreciates, the 20×GT buffer would be diluted to 1× in the final reaction mix.

The PCR primers should be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art appreciates how to select appropriate PCR primer pairs to amplify the target nucleic acid analyte of interest.

In a third embodiment, a homogenous assay may be performed such as real-time PCR, for example. In this assay, the labeled nucleic acid probe contains a stretch of nucleic acid sequences that are capable of recognizing 8-mer and 9-mer motifs in the target nucleic acid analyte, as described above. FRET quenching of the labeled nucleic acid probe is irrevocably eliminated when the Taq polymerase reaches the region where the labeled probe is annealed to the target nucleic acid analyte, recognizes the probe-template hybrid as a substrate, and subsequently hydrolyzes phosphodiester bonds of the probe during primer-directed DNA amplification. The hydrolysis reaction irrevocably releases the quenching effect of the quencher dye on the reporter dye, thus resulting in increasing detector fluorescence with each successive PCR cycle. It will be appreciated that the invention is not limited to the use of real-time PCR, and that other variations of PCR, described above, may be used to detect and/or quantify the analyte of interest.

As noted above, the homogenous assay of the invention should not be construed to be limited to PCR-based detection methods, but may employ any method of detection and/or quantification to detect and/or quantify a target nucleic acid analyte. In one aspect, PCR may be used to amplify a target. In another aspect, other amplification systems or detection systems may be used, including systems described in U.S. Pat. No. 7,118,910, which is incorporated herein by reference in its entirety. In a further aspect, a detection system other than PCR may be used such as an Invader® assay (Third Wave, Madison, Wis.). In one aspect, real time quantification methods may be used to determine the quantity of a target nucleic acid analyte present in a sample by measuring the amount of amplification product formed during or after the amplification process itself. Fluorogenic nuclease assays are one specific example of a real time quantification method that may be used successfully with the matrix-type microfluidic devices described herein. This method of monitoring the formation of amplification product involves the continuous measurement of PCR product accumulation using a dual-labeled nucleic acid probe, such as a hydrolysis probe. It will be appreciated that the invention is not limited to use of these probes and any tag-specific probe may be used.

In a fourth embodiment, the aliquots in the reaction chambers may be queried for the presence of the targeted nucleic acid analyte, which is accomplished by the use of the labeled probes. The fluorescent signal may be monitored and quantified with fluorescence detectors, such as fluorescence spectrophotometers and commercial systems that allow the monitoring of fluorescence in PCR reactions.

Alternatively, however, the probe may be unlabeled, but may be detectable by specific binding with a ligand which is labeled, either directly or indirectly. Suitable labels, and method for labeling probes and ligands are well known in the art, and include, for example, radioactive labels which may be incorporated by known methods (e.g., nick translation, random priming or kinasing), biotin, fluorescent groups, chemiluminescent groups (e.g., dioxetanes) enzymes, antibodies, gold nanoparticles and the like. Variations of this basic scheme are known in the art, and include those variations that facilitate separation of the hybrids to be detected from extraneous materials and/or that amplify the signal from the labeled moiety.

It will be appreciated that specifically at least about 10, more often at least about 25, still more often at least about 50, even more often at least about 100, in some cases at least about 500 and sometimes at least about 1000 targets may be detected using the methodology of the invention. Thus, the method may make use of at least about 10, more often at least about 25, still more often at least about 50, even more often at least about 100, in some cases at least about 500 and sometimes at least about 1000 target-specific probes. Additional details about systems and methods of conducting PCR reactions and analyzing reaction contents in microfluidic systems are described in U.S. patent application Ser. No. 61/044,417 to Facer et al., titled "Multilevel Microfluidic Systems and Methods," filed on Apr. 11, 2008, the entire contents of which are herein incorporated by reference for all purposes.

2. Crystal Growth and Analysis Applications

Crystallization is an important technique to the biological and chemical arts. Specifically, a high-quality crystal of a target compound can be analyzed by x-ray diffraction techniques to produce an accurate three-dimensional structure of the target. This three-dimensional structure information can then be utilized to predict the functionality and behavior of the target. Unfortunately however, growing high-quality crystals is usually a very difficult, and sometimes impossible, process that requires a lot of trial and error. Particularly for biological compounds, their highly complex and irregular structures make it difficult to form them into a highly ordered crystal structure.

The challenges for growing high-quality crystals has been addressed with systems and methods for high throughput screening of target materials for crystallization growth potential using microfluidic systems. High throughput screening of crystallization of target material, or purification of small samples of target material by recrystallization, may be accomplished by simultaneously introducing a solution of the target material at known concentrations into one or more reaction chambers of a microfabricated fluidic system. The microfluidic system may then be manipulated to vary solution conditions in the reaction chamber to provide a crystallization environment. Control over the changed solvent conditions may result from a variety of techniques, including but not limited to metering of volumes of a crystallizing agent into the chamber by volume exclusion, by entrapment of liquid volumes determined by the dimensions of the microfabicated structure, or by cross-channel injection into a matrix of junctions defined by intersecting orthogonal flow channels, among other techniques. Additional description of crystallization techniques and systems may be found in U.S. Pat. No. 7,052,545 to Quake et al., titled "High Throughput Screening of Crystallization of Materials," the entire contents of which is herein incorporated by reference for all purposes.

Crystals resulting from crystallization in accordance with embodiments of the present invention can be utilized for x-ray crystallography to determine three-dimensional molecular structure. Promising screening results can also be utilized as a basis for further screening focusing on a narrower spectrum of crystallization conditions, in a manner, for example, analogous to the use of standardized sparse matrix techniques.

The crystallization systems and methods in accordance with embodiments of the present invention may be particular suited to crystallizing larger biological macromolecules or aggregates thereof, such as proteins, nucleic acids, viruses, and protein/ligand complexes. However, methods and systems are not limited to any particular type of target material.

When crystallization conditions are favorable, crystals can often grow to sizes too large to leave the microfluidic reaction chamber through microfluidic flow channels. Embodiments of the present invention can recover these crystals by partially or completely peeling off the peelable cover, exposing the reaction chamber and permitting access by crystal extraction equipment (e.g., tweezers). The crystals may then be moved intact to other equipment for testing and analysis.

Figure 13:
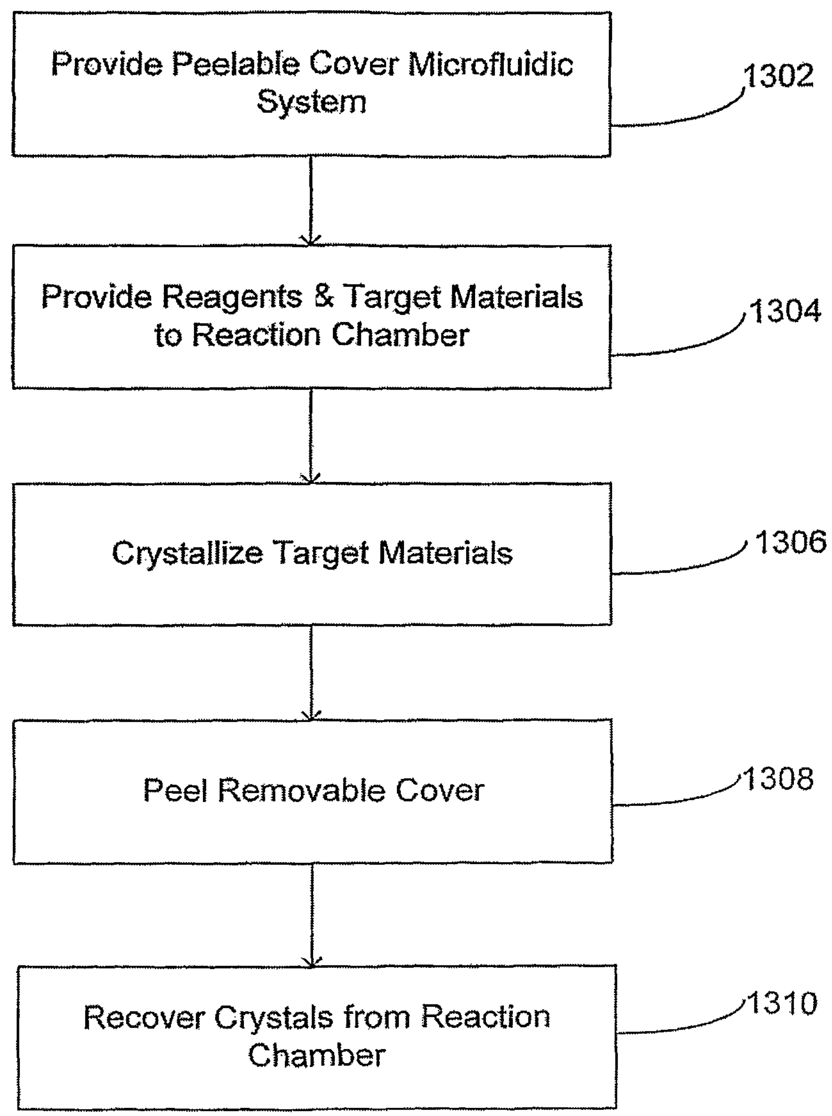
FIG. 13 shows selected steps in a method of forming and recovering crystallized reaction products from a peelable cover microfluidic system according to embodiments of the invention.

Referring now to FIG. 13, a flowchart is shown with selected steps in a method of making and recovering crystallization reaction products from a peelable cover microfluidic systems according to embodiments of the invention. The method may include providing a peelable cover microfluidic reaction system 1302 that includes or is coupled to reagents for crystallizing a target materials. The reagents and target material may be provided to a reaction chamber 1304 where crystallization of the target materials 1306 is performed. As noted above, techniques to crystallize the target material may include changing solvent conditions by metering of volumes of a crystallizing agent into the chamber by volume exclusion, by entrapment of liquid volumes determined by the dimensions of the microfabricated structure, or by cross-channel injection into a matrix of junctions defined by intersecting orthogonal flow channels, among other techniques.

The removable over may then be partially peeled back or completely peeled off 1308 to expose at least a portion of the reaction chamber and crystals. The crystals may then be recovered 1310 through the opening, in some embodiments with the help of crystal extraction tools.

Exemplary Systems for Removal of A Planar Component from Microfluidic Device

Systems and methods are described to remove the peelable cover without affecting products in microfluidic chambers. Furthermore, removal of an integrated Head Spreader (IHS) from an Integrated Fluidic Circuit (IFC) array device is often a challenge because of induced bubbles in sample chambers from a manual peeling action. Such occurrence of bubbles have been observed across the chambers of the IFC device. More than 80% of the sample chambers may reveal bubbles after the IHS is removed. Residue may be seen on the removed IHS, suggesting a possible loss of valuable products from the sample chamber.

Figure 14:
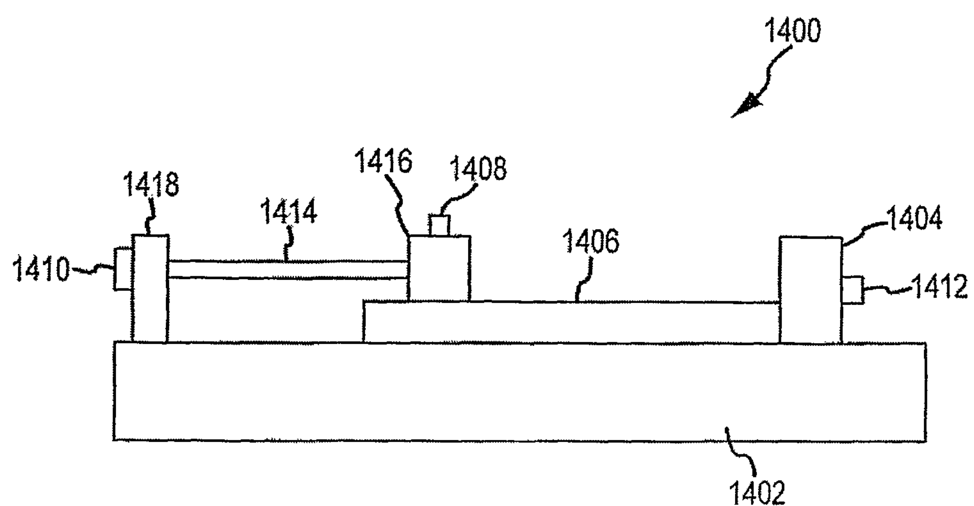
FIG. 14 shows a simplified cross-sectional view of a fixture for peeling off a removable component from a microfluidic assembly according to an embodiment of the present invention.
Figure 15:
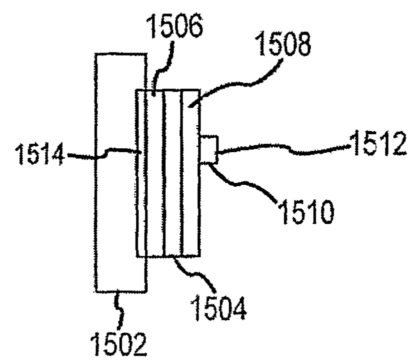
FIG. 15 shows a simplified side view of a microfluidic assembly having a removable component.
Figure 16:
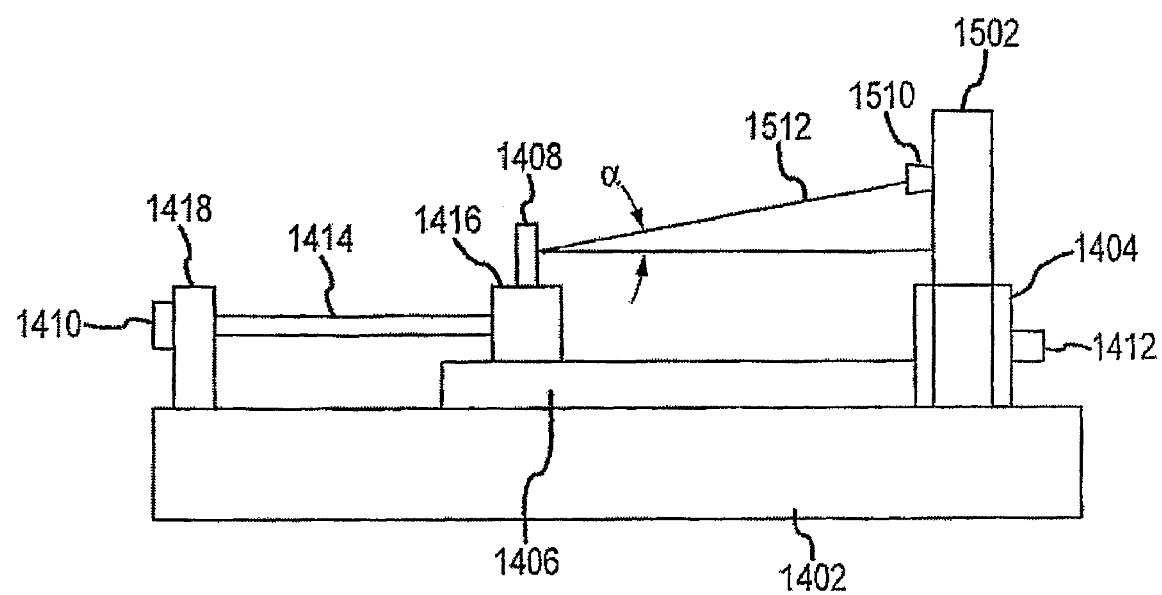
FIG. 16 shows a simplified cross-sectional view of a fixture that holds a removable component from a microfluidic assembly according to an embodiment of the present invention.

FIG. 14 illustrates a fixture 1400 for assisting removal of a component from a microfluidic assembly. The removable component may be a peelable cover, or a IHS. The fixture 1400 includes a carrier holder 1404 that has a hollow portion and sidewalls. A slider 1406 is attached to the carrier holder 1404 and mounted on a supporting substrate 1402. A movable block 1416 is positioned on top of the slider 1406 and may be moved by using a lead screw 1410 through a shaft 1414. The lead screw 1410 connects to the shaft 1414 through a fixed block 1418 that is mounted to the supporting substrate 1402. By turning the lead screw 1410, the movable block 1416 may be moved relative to the slider 1406. A line hook 1408 is mounted on the movable block 1416. A fastening component 1412 is positioned on one of the sidewalls to secure a device disposed in the holder 1404. According to an embodiment of the present invention, the device may be a microfluidic assembly 1500 as illustrated in FIG. 15. FIG. 16 illustrates the fixture 1400 that holds the microfluidic assembly including a carrier 1502 with a chip 1514 in a carrier slot 1404.

The microfluidic assembly 1500 is illustrated in FIG. 15. The microfluidic assembly 1500 includes a microfluidic carrier 1502 with a chip 1514, and a removable component 1506 attached to the chip 1514. The assembly 1500 also includes a double side adhesive sheet 1504 bonded to the removable component 1506. A plastic cover plate 1508 is bonded to the other side of the adhesive sheet 1504. A hooking component 1510 for holding a tension wire 1512 is configured to attach to the plastic cover plate 1508 and the adhesive sheet 1504. Areas of the cover plate 1508 and adhesive sheet 1504 are smaller than the carrier 1502, but close to that of the chip 1514.

FIG. 16 illustrates a fixture 1400 that holds a carrier 1502 with a chip 1514 in a carrier slot 1404. The carrier 1502 is secured in the carrier slot 1404 by using a fastening component 1412. There is an angle α formed between a horizontal plane and the tension wire 1512 that connects the line hook 1408 and the hooking component 1510. The hooking component 1510 can be pulled through the tension wire 1512 by adjusting the lead screw 1410 through the shaft 1414 to move the movable block 1416 relative to the slider 1406.

Figure 17:
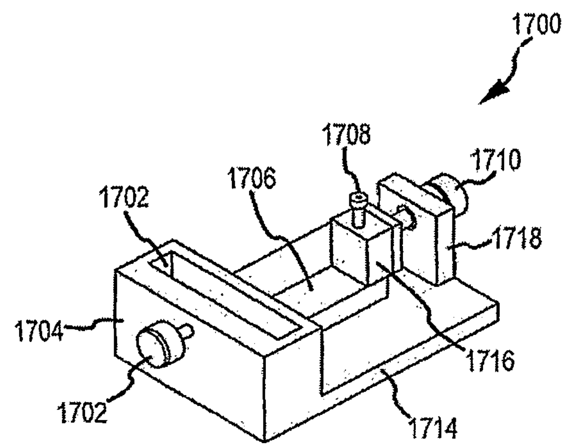
FIG. 17 shows one simplified 3-D view for a fixture for peeling off a removable component from a microfluidic assembly according to an embodiment of the present invention.

FIG. 17 illustrates a 3-dimensional view of an exemplary fixture 1700 according to one embodiment of the present invention. The fixture 1700 includes a carrier holder 1704, a slider 1706 attached to the carrier holder 1704 and supporting substrate 1714, and a line hook 1708 attached to a movable block 1716 that is slidable relative to the slider 1706. The fixture also includes a carrier slot 1712 in the carrier holder 1704, a carrier secure knob 1702 mounted to a sidewall of the carrier holder 1704, and a tension pull knob 1710 mounted to a holding block 1718 attached to a supporting substrate 1714. The tension pull knob 1710 is coupled to the movable block 1716. By turning the tension pull knob 1710, the line hook 1708 can be moved relative to the carrier slot 1712. In this specific embodiment, the supporting substrate 1714 may be integrated with the carrier holder 1704, as illustrated.

Figure 18:
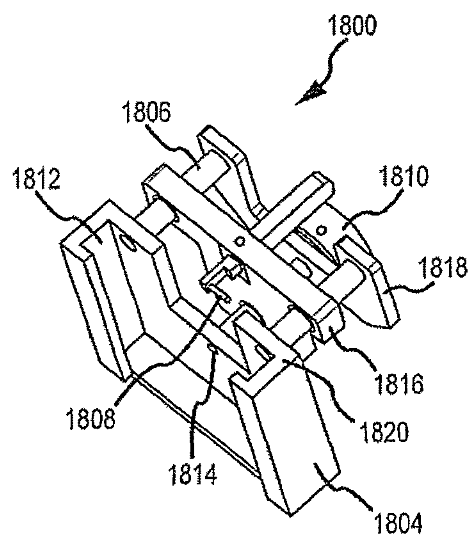
FIG. 18 shows another simplified 3-D view for a fixture for peeling off a removable component from a microfluidic assembly according to an alternative embodiment of the present invention.

FIG. 18 illustrates a 3-dimensional view of an alternative fixture 1800 according to another embodiment of the present invention. The alternative fixture 1800 includes a carrier holder 1804 that has a carrier slot 1812. The alternative fixture 1800 also includes sliders 1806, each of the sliders 1806 is attached to a sidewall 1820 of the carrier holder 1804. The sidewall 1820 has an open portion that allows a removable component such as IHS to be removed from a chip 1514 of the carrier 1502 disposed in the carrier slot 1812. A line hook 1808 is positioned near the open portion of the sidewall 1820 and attached to a movable block 1816 that is slidable on the slider 1806. A tension pull knob 1810 is attached a fixed block 1818 and coupled to the movable block 1816 through a shaft 1814. By adjusting the tension pull knob 1810, the line hook 1808 can be moved relative to the carrier slot 1812.

Experiments have been performed by using the fixture as illustrated in FIG. 17. Results show that peeling of IHS was 99% bubble free on chips loaded with TE buffer and actual PCR chemistry. FIGS. 20*a-d* show the photographs of the actual device used in Fluidigm. After completion of PCR, a plastic plate is attached to an IHS on an underside of a carrier chip using an industrial grade double side tape. A tension wire is attached to the plastic plate and the adhesive tape. The tension wire may be made of a metal or a plastic that has a tensile strength high enough to peel the IHS or any removable component off the carrier chip.

Figure 19:
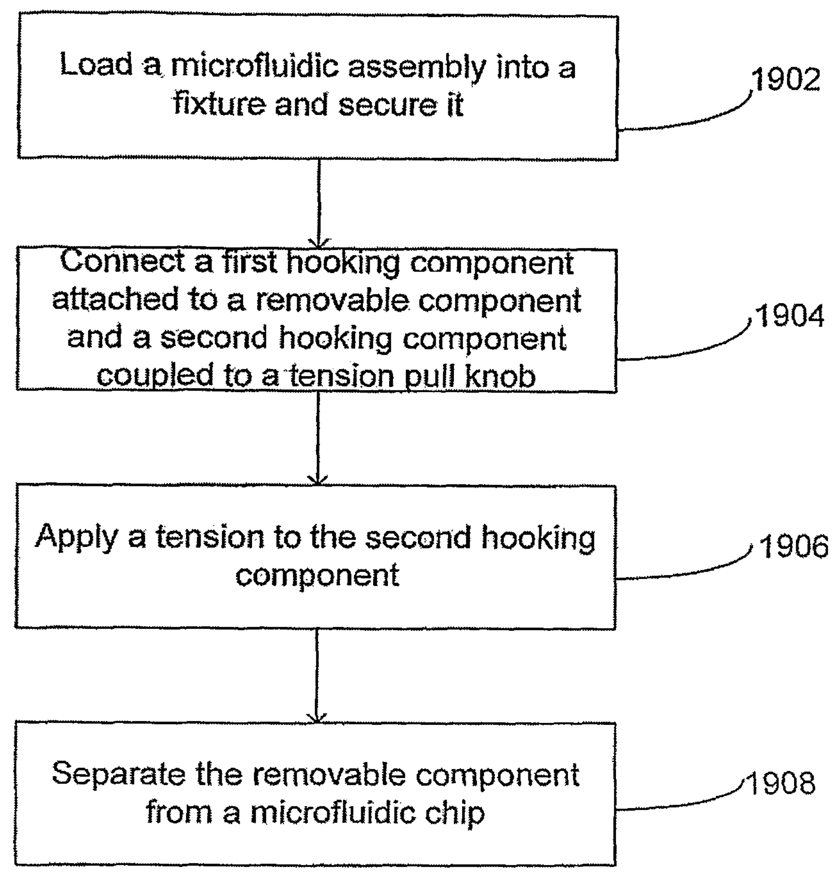
FIG. 19 is a flow chart illustrating selected steps in a method of peeling off a removable component from a microfluidic assembly.

FIG. 19 is a flow chart illustrating selected steps in methods of peeling a removable component from a microfluidic assembly according to embodiments of the invention. The methods may include loading a microfluidic assembly 1902 in a fixture. The microfluidic assembly may comprise a carrier, a microfluidic chip on the carrier, a removable component attached to the microfluidic chip, and an adhesive sheet bonded to the removable component and a cover plate. The removable component includes, but not limited to an Integrated Heater Spreader (IHS) and a peelable cover. The removable component may be planar or non-planar. The carrier may include wells, chambers, channels, fluid reservoirs, fluid inlets, and/or other components that are in fluid communications with the microfluidic chip. The microfluidic chip may also include structures for flow channels, control channels, fluid reservoirs, and/or other components that may also be formed in various elastomeric layers.

Embodiments of the microfluidic assembly include the cover plate or a layer of semi-rigid plastic, such as a layer of poly(ethylene terephthalate) (PET), the cover plate glued to the removable component by an adhesive sheet sandwiched between the removable component and the cover plate (e.g., a transparent adhesive such as Optically Clear Laminating Adhesive 8142 from the Minnesota Mining and Manufacturing Co.), the removable component attached to the microfluidic chip on the carrier. A first hooking component is coupled to the cover plate and adhesive sheet such that the first hooking component may peel the removable component off the microfluidic chip.

The fixture includes a carrier holder that has a carrier slot, and a fastening component coupled to the carrier slot for securing the microfluidic assembly in the carrier slot. The fixture also includes a movable block with a second hooking component. The movable block may slide on a slider that may be attached to the carrier holder or a supporting substrate that is attached to the carrier holder. The movable block may be moved by a tension pull knob through a shaft connected to the movable block. The tension pull knob and the shaft are coupled to a fixed block that may be attached to a supporting substrate or to the carrier holder.

Following loading the microfluidic assembly in the carrier slot and securing it, the method includes connecting a first hooking component to a second hooking component using a tension wire at step 1904. In additional embodiments, the method further includes applying a tension to the second hooking component while trying to keep the tension at a minimal by slowly turning the tension pull knob at step 1906. The entire peeling process may take approximately 6 minutes, rather than a quick peeling off.

When the removable component is separated at step 1908 (e.g., peeled off) from the microfluidic chip or an underlying elastomeric structure, the removable component such as IHS will stay bonded to the cover plate. As a result, less bubbles are produced in sample chambers on the microfluidic chip.

FIG. 20*a* illustrates an embodiment of the attachment of a hooking component to the adhesive sheet with the cover plate. Such attachment is through wrapping an end of the tension wire into and out of holes in the adhesive sheet and the cover plate. The hooking component is actually part of the tension wire and is positioned along a center line and toward a top edge of the adhesive and cover plate. FIG. 20*b* illustrates that the adhesive sheet and cover plate are attached to the IHS and are secured to the IHS.

FIG. 20*c* illustrates that the carrier with microfluidic chip is mounted and secured in the fixture. FIG. 20*c* also illustrates that tension wire is hooked onto the fixture's line hook. The lead screw can be turned to increase tension in the tension wire, which in turn, pulls the IHS off from the microfluidic chip. Such action of turning screw may be manually controlled by an operator at a minimal tension force through the entire peel process. In a specific embodiment of the invention, the lead screw may be turned by a motor. A low tension force and slow turning of the lead screw are necessary conditions to keep bubble occurrence to a minimal level. Moreover, the tension wire has an angle from a horizontal plane. The angle may vary depending upon the variations in a fixture.

FIG. 20*d* illustrates a condition after the IHS is removed from the carrier chip. In this particular embodiment, the top edge is first peeled off and the bottom edge is last peeled off. In an alternative embodiment, all edges may be peeled off simultaneously, depending upon how the tension wire is hooked to the adhesive sheet and cover plate as well as the angle of the tension wire from the horizontal plane.

It is understood that the invention is not limited to the particular materials, designs, production methods, protocols, and reagents, etc., described herein, as these may vary as the skilled artisan will recognize. It is also to be understood that the terminology used herein is used for the purpose of describing particular embodiments only, and is not intended to limit the scope of the invention. It is also to be noted that as used herein and in the appended claims, the singular forms "a," "an," and "the" include the plural reference unless the context clearly dictates otherwise. Thus, for example, a reference to "a reaction chamber" is a reference to one or more chambers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A microfluidic system comprising:

a base substrate;

a sample holding layer formed on the base substrate, wherein the sample holding layer comprises a microfabricated cavity having an opening formed on a surface of the layer that faces opposite the substrate;

a flow channel coupled to the cavity for delivering a reagent to the cavity;

a control channel that intersects the flow channel and forms a deflectable membrane over at least a portion of the intersection, wherein actuation of the control channel causes deflection of the deflectable membrane to open or close the flow channel; and a removable cover having a cover layer with a first portion and a second portion, wherein the first portion and the second portion of the cover layer are coplanar when the cover layer is situated on the surface of the sample holding layer that faces opposite the substrate, and wherein the first portion of the cover layer is removable from the second portion of the cover layer to expose at least part of the opening in the microfabricated cavity while the second portion of the cover layer remains bonded to the sample holding layer.

2. The microfluidic system of claim 1, wherein the sample holding layer comprises an elastomeric material.

3. The microfluidic system of claim 1, wherein the sample holding layer comprises a non-elastomeric material.

4. The microfluidic system of claim 3, wherein the non-elastomeric material comprises glass.

5. The microfluidic system of claim 1, wherein at least part of the flow channel is formed in the sample holding layer.

6. The microfluidic system of claim 1, wherein the control channel is formed in the sample holding layer.

7. The microfluidic system of claim 1, wherein the microfabricated cavity is a reaction chamber.

8. The microfluidic system of claim 1, wherein the cover layer of the removable cover is a first elastomeric layer bonded to the sample holding layer, and the removable cover further comprises a second thermoplastic layer bonded to the first elastomeric layer by an adhesive layer.

9. The microfluidic system of claim 8, wherein the sample holding layer comprises the same material as the first elastomeric layer of the removable cover.

10. The microfluidic system of claim 8, wherein the second portion of the cover layer comprises a portion of the first elastomeric layer of the removable cover that does not overlap with the opening in the microfabricated cavity and that remains bonded to the sample holding layer after the first portion of the cover layer is removed from the second portion of the cover layer to expose at least part of the opening.

11. The microfluidic system of claim 8, wherein the first portion of the cover layer comprises a portion of the first elastomeric layer that overlaps with the opening in the microfabricated cavity and that remains bonded to the second thermoplastic layer when the cover is removed from the sample holding layer.

12. The microfluidic system of claim 8, wherein the first elastomeric layer comprises PDMS.

13. The microfluidic system of claim 8, wherein the second thermoplastic layer comprises PET.

14. The microfluidic system of claim 8, wherein the adhesive layer comprises an acrylic adhesive.

15. The microfluidic system of claim 1, wherein the base substrate comprises a rigid material.

16. The microfluidic system of claim 15, wherein the rigid material comprises glass.

17. The microfluidic system of claim 1, wherein the cavity has a volume ranging from 1 nL to 100 nL.

18. The microfluidic system of claim 1, wherein the sample holding layer comprises the same material as the cover layer of the removable cover.

19. The microfluidic system of claim 1, wherein the first portion of the cover layer overlaps with the opening in the microfabricated cavity and the second portion of the cover layer does not overlap with the opening in the microfabricated cavity.

20. The microfluidic system of claim 1, wherein the cover layer of the removable cover comprises PDMS.

21. A method of microfabricating a microfluidic system with a removable cover, the method comprising:

providing a base substrate;

bonding a sample holding layer to the base substrate, wherein the sample holding layer comprises a microfabricated cavity or recess having an opening formed on a surface of the layer that faces opposite the substrate;

microfabricating a flow channel coupled to the cavity for delivering a reagent to the cavity;

microfabricating a control channel that intersects the flow channel and forms a deflectable membrane to open or close the flow channel, wherein actuation of the control channel causes deflection of the deflectable membrane to open or close the flow channel; and bonding a removable cover to the sample holding layer for sealing the cavity, the removable cover having a cover layer with a first portion and a second portion, wherein the first portion and the second portion of the cover layer are coplanar when the cover layer is situated on the surface of the sample holding layer that faces opposite the substrate, and wherein the first portion of the cover layer is removable from the second portion of the cover layer to expose at least part of the opening in the microfabricated cavity while the second portion of the cover layer remains bonded to the sample holding layer.

22. The method of claim 21, wherein the cover layer of the removable cover is a first elastomeric layer and the removable cover further comprises a second thermoplastic layer, the method further comprising:

bonding the second portion of the cover layer to the sample holding layer; and bonding the second thermoplastic layer to the first elastomeric layer with an adhesive layer.

23. The method of claim 22, wherein the first portion of the cover layer comprises a portion of the first elastomeric layer that overlaps with the opening in the microfabricated cavity and that remains bonded to the second thermoplastic layer when the cover is removed from the sample holding layer.

24. The method of claim 22, wherein the second portion of the cover layer comprises a portion of the first elastomeric layer of the removable cover that does not overlap with the opening in the microfabricated cavity remains bonded to the sample holding layer after the first portion of the cover layer is removed from the second portion of the cover layer to expose at least part of the opening.

25. The method of claim 22, wherein the sample holding layer comprises the same elastomeric material as the first elastomeric layer of the removable cover.

26. The method of claim 25, wherein the first elastomeric layer comprises PDMS.

27. The method of claim 21, wherein the microfabricated cavity is a reaction chamber.

28. The method of claim 21, wherein the base substrate comprises a rigid material.

29. The method of claim 28, wherein the rigid material comprises glass.

30. The method of claim 21, wherein the sample holding layer comprises the same material as the cover layer of the removable cover.

31. The method of claim 21, wherein the cover layer of the removable cover comprises PDMS.

* * * * *